US009259468B2

(12) United States Patent
Gesguiere et al.

(10) Patent No.: US 9,259,468 B2
(45) Date of Patent: Feb. 16, 2016

(54) CANCER THERAPY VIA SELECTIVE UPTAKE OF SPECIALIZED NANOPARTICLES IN CANCER CELLS

(71) Applicant: University of Central Florida Research Foundation, Inc., Orlando, FL (US)

(72) Inventors: Andre Gesguiere, Chuluota, FL (US); Mona Mathew, Orlando, FL (US); Zhongjian Hu, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 572 days.

(21) Appl. No.: 13/647,506

(22) Filed: Oct. 9, 2012

(65) Prior Publication Data

US 2013/0129664 A1 May 23, 2013

Related U.S. Application Data

(60) Provisional application No. 61/544,312, filed on Oct. 7, 2011.

(51) Int. Cl.
*A61K 41/00* (2006.01)
*A61K 47/48* (2006.01)
*B82Y 5/00* (2011.01)

(52) U.S. Cl.
CPC ........... *A61K 41/0057* (2013.01); *A61K 47/489* (2013.01); *A61K 47/48884* (2013.01); *A61K 47/48961* (2013.01); *B82Y 5/00* (2013.01)

(58) Field of Classification Search
CPC .................. A61K 47/48884; A61K 47/48961; A61K 41/0057; A61K 47/489; B82Y 5/00
See application file for complete search history.

(56) References Cited

U.S. PATENT DOCUMENTS

2009/0169613 A1* 7/2009 Reznik et al. ................. 424/450

OTHER PUBLICATIONS

Liu, Jian, et al. "Preparation of PEG-conjugated fullerene containing Gd 3+ ions for photodynamic therapy." Journal of controlled release 117.1 (2007): 104-110.*
Tabata, Yasuhiko, Yoshiyuki Murakami, and Yoshito Ikada. "Photodynamic Effect of Polyethylene Glycol-modified Fullerene on Tumor." Cancer Science 88.11 (1997): 1108-1116.*
Yu, Chi, et al. "Efficiency of singlet oxygen production from self-assembled nanospheres of molecular micelle-like photosensitizers FC 4 S." Journal of Materials Chemistry 15.18 (2005): 1857-1864.*
Howes, Philip, et al. "Phospholipid encapsulated semiconducting polymer nanoparticles: their use in cell imaging and protein attachment." Journal of the American Chemical Society 132.11 (2010): 3989-3996.*
Hu, Z. J. et al., "Correlation between spectroscopic and morphological properties of composite P3HT/CBM nanoparticles studied by single particle spectroscopy", Journal of Luminescence, 2010, vol. 130, pp. 771-780.
Tenery, D. et al., "Single particle spectroscopy on composite MEH-PPV/PCBM nanoparticles", Journal of Luminescence, 2009, vol. 129, pp. 423-429.
Tenery, D. et al., "Interplay between fluorescence and morphology in composite MEH-PPV/PCBM nanoparticles studied at the single particle level", Chemical Physics, 2009, vol. 365, pp. 138-143.
Tenery, D. et al., "Effect of PCBM Concentration on Photoluminescence Properties of Composite MEH-PPV/PCBM Nanoparticles Investigated by a Franck-Condon Analysis of Single-Particle Emission Spectra", Chemphyschem, 2009, vol. 10, pp. 2449-2457.
Hu, Z. J. et al., "PCBM concentration dependent morphology of P3HT in composite P3HT/PCBM nanoparticles", Chemical Physics Letters, 2009, vol. 476, pp. 51-55.
Gesquiere, A. J. et al., "Single-Particle Spectroscopy on Conducting Polymer-Fullerene Composite Material for Application in Organic Photovoltaic Devices", Spectroscopy 2008, vol. 23, pp. 32-38.
http://health.usnews.com/best-hospitals/rankings/cancer 2011, US News, downloaded Jun. 17, 2015, 4 pages.
American Cancer Society "Cancer Facts & Figures", 2011, 60 pages.
Diamandopoulus, G. T., "Cancer: An Historical Perspecitve", Anticancer Res., 1996, vol. 16, pp. 1596-1602.
Sayes, C. M. et al., "Nano-C60 cytotoxicity is due to lipid peroxidation", Biomaterials, 2005, vol. 26, pp. 7587-7595.
Howes, P. et al., "Phospholipid Encapsulated Semiconducting Polymer Nanoparticles: Their Use in Cell Imaging and Protein Attachment", J Am Chem Soc, 2010, vol. 132, pp. 3989-3995.
Siddiquee, K. et al., "Selective chemical probe inhibitor of Stat3, identified through structure-based virtual screening, induces antitumor activity", Proceedings of the National Academy of Sciences of the United States of America, 2007, vol. 104, pp. 7391-7396.
Turkson, J. et al., "Inhibition of constitutive signal transducer and activator of transcription 3 activation by novel platinum complexes with potent antitumor activity", Molecular Cancer Therapeutics, 2004, vol. 3, pp. 1533-1542.
Grimland, J. L. et al., "Photosensitizer-doped conjugated polymer nanoparticles with high cross-sections for one- and two-photon excitation", Nanoscale, 2011, vol. 3, pp. 1451-1455.
Harewood, G. C.et al., "Pilot study to assess patient outcomes following endoscopic application of photodynamic therapy for advanced cholangiocarcinoma",J. Gastroenterol. Hepatol., 2005, vol. 20, pp. 415-420.
Mlkvy, P. et al., "Photodynamic therapy for gastrointestinal tumors using three photosensitizers—ALA induced PPIX Photofrin and MTHPC. A pilot study", Neoplasma, 1998, vol. 45, pp. 157-161.
Overholt, B. F. et al., "Photodynamic therapy for Barrett's esophagus: follow-up in 100 patients", Gastrointestinal Endoscopy, 1999, vol. 49, pp. 1-7.
Choi, H. S. et al., "Design Considerations for Tumor-Targeted Nanoparticles", Nature Nanotechnology, 2010, vol. 5, pp. 42-47.

(Continued)

*Primary Examiner* — Abigail Fisher
*Assistant Examiner* — Daniel L Branson
(74) *Attorney, Agent, or Firm* — Timothy H. Van Dyke; Beusse, Wolter, Sanks & Maire, PLLC

(57) ABSTRACT

Disclosed herein are polymer/fullerene nanoparticles that have selective uptake into cancer cells, and which, upon being taken into the cancer cells induce apoptosis. Induction of apoptosis can be controlled by activation of the nanoparticles. Activation can occur such as by photoactivation, or other means.

5 Claims, 13 Drawing Sheets

(56) References Cited

OTHER PUBLICATIONS

Droge, W., "Free Radicals in the Physiological Control of Cell Function", Physiological Reviews 2002, vol. 82, pp. 47-96.
Valko, M.et al., "Free radicals and antioxidants in normal physiological functions and human disease", International Journal of Biochemistry & Cell Biology, 2007, vol. 39, pp. 44-84.
Valko, M. et al., "Free radicals, metals and antioxidants in oxidative stress-induced cancer", Chemico-Biological Interactions, 2006, vol. 160, pp. 1-40.
Wallace, D. C., "A mitochondrial paradigm of metabolic and degenerative diseases, aging, and cancer: A dawn for evolutionary medicine", in Annual Review of Genetics, 2005; vol. 39; pp. 359-409.
Cantley, L. C., "The Phosphoinositide 3-Kinase Pathway", Science, 2002, vol. 296, pp. 1655-1657.
Downward, J., "Targeting RAS Signalling Pathways in Cancer Therapy", Nature Reviews Cancer, 2003, vol. 3, pp. 11-22.
Karin, M. et al., "NF-$_{\kappa}$B in Cancer: From Innocent Bystander to Major Culprit", Nature Reviews Cancer 2002, vol. 2, pp. 301-310.
Wilhelm, S. M. et al., "BAY 43/9006 Exhibits Broad Spectrum Oral Antitumor Activity and Targets the RAF/MEK/ERK Pathway and Receptor Tyrosine Kinases Involved in Tumor", Cancer Research, 2004, vol. 64, pp. 7099-7109.
Manning, B. D. et al., "AKT/PKB Signaling: Navigating Downstream", Cell, 2007, vol. 129, pp. 1261-1274.
Vivanco, I. et al., "The Phosphatidylinositol 3-Kinase-AKT Pathway in Human Cancer", Nature Reviews Cancer, 2002, vol. 2, pp. 489-501.
Engelman, J. A. et al., "MET Amplification Leads to Gefitinib Resistance in Lung Cancer by Activating ERBB3 Signaling", Science, 2007, vol. 316, pp. 1039-1043.
Hennessy, B. T. et al., "Exploiting the PI3K/AKT Pathway for Cancer Drug Discovery", Nature Reviews Drug Discovery, 2005, vol. 4, pp. 988-1004.
Elstrom, R. L. et al., "Akt Stimulates Aerobic Glycolysis in Cancer Cells", Cancer Research, 2004, vol. 64, pp. 3892-3899.
Nogueira, V. et al., "Akt determines replicative senescence and oxidative or oncogenic premature senescence and sensitizes cells to oxidative apoptosis", Cancer Cell, 2008, vol. 14, pp. 458-470.
Robey, R. B. et al, "Mitochondrial hexokinases, novel mediators of the antiapoptotic effects of growth factors and Akt", Oncogene, 2006, vol. 25, pp. 4683-4696.
Tsuruo, T. et al., "Molecular targeting therapy of cancer: drug resistance, apoptosis and survival signal", Cancer Science, 2003, vol. 94, pp. 15-21.
Fariss, M. W. et al., "Role of Mitochondria in Toxic Oxidative Stress", Molecular Interventions, 2005, vol. 5, pp. 94-111.
Alscher, R. G.et al., "Reactive oxygen species and antioxidants: Relationships in green cells", Physiologia Plantarum, 1997, vol. 100, pp. 224-233.
Baynes, J. W., "Role of Oxidative Stress in Development of Complications in Diabetes", Diabetes, 1991, vol. 40, pp. 405-412.
Baynes, J. W. et al., "Role of Oxidative Stress in Diabetic Complications a New Perspective on an Old Paradigm", Diabetes, 1999, vol. 48, pp. 1-9.
Blokhina, O. et al., "Antioxidants, Oxidative Damage and and Oxygen Deprivation Stress: A Review", Annals of Botany, 2003, vol. 91, pp. 179-194.
Dandona, P. et al., "Oxidative Damage to DNA in Diabetes Mellitus", Lancet, 1996, vol. 347, pp. 444-445.
Floyd, R. A., "Antioxidants, Oxidative Stress and Degenerative Neurological Disorders", Proceedings of the Society for Experimental Biology and Medicine, 1999, vol. 222, pp. 236-245.
Galvez-Valdivieso, G. et al., "The role of reactive oxygen species in signalling from chloroplasts to the nucleus". Physiologia Plantarum, 2010, vol. 138, 430-430/.
Hancock, J. T. et al., "Role of reactive oxygen species in cell signalling pathways", Biochemical Society Transactions, 2001, vol. 29, pp. 345-350.
Hensley, K. et al., "Reactive Oxygen Species, Cell Signaling, and Cell Injury", Free Radical Biology and Medicine, 2000, vol. 28, pp. 1456-1462.
Kamata, H.et al., "Redox Regulation of Cellular Signalling", Cellular Signalling, 1999, vol. 11, pp. 1-14.
Liou, G. Y. et al., "Reactive oxygen species in cancer", Free Radical Research, 2010, vol. 44, pp. 479-511.
Riley, P. A., "Free radicals in Biology: oxidative stress and the effects of ionizing radiation", International Journal of Radiation Biology, 1994, vol. 65, pp. 27-33.
Simonian, N. A. et al., "Oxidative Stress in Neurodegenerative Diseases", Annual Review of Pharmacology and Toxicology, 1996, vol. 36, pp. 83-106.
Thannickal, V. J. et al., "Reactive oxygen species in cell signaling", American Journal of Physiology-Lung Cellular and Molecular Physiology, 2000, vol. 279, pp. L1005-L1028.
Zhou, H. et al., "Oxidative Stress and Apoptosis of Human Brain Microvascular Endothelial Cells Induced by Free Fatty Acids", Journal of International Medical Research, 2009, vol. 37, pp. 1897-1903.
Trachoothan, D. et al., "Targeting cancer cells by ROS-mediated mechanisms: a radical therapeutic approach?", Nature Reviews Drug Discovery, 2009, vol. 8, pp. 579-591.
Trachootham, D. et al., "Selectivekillingofoncogenically transformedcells through aROSmediated mechanism by b-phenylethyl isothiocyanate", Cancer Cell, 2006, vol. 10, pp. 241-252.
Chan, W. et al., "CdSe quantum dots induce apoptosis in human neuroblastoma cells via mitochondrial-dependent pathways and inhibition of survival signals", Toxicology Letters, 2006, vol. 167, pp. 191-200.
Chen, J. et al., "Quantum Dot-mediated Photoproduction of Reactive Oxygen Species for Cancer Cell Annihilation", Photochemistry and Photobiology, 2010, vol. 86, pp. 431-437.
Cho, S. J. et al., "Long-Term Exposure to CdTe Quantum Dots Causes Functional Impairments in Live Cells", Langmuir, 2007,vol. 23, pp. 1974-1980.
Ito, S. et al., "Enhancement of 5-Aminolevulinic acid-induced oxidative stress on two cancer cell lines by gold nanoparticles", Free Radical Research, 2009, vol. 43, pp. 1214-1224.
Li, K. G. et al., "Intracellular oxidative stress and cadmium ions release induce cytotoxicity of unmodified cadmium sulfide quantum dots", Toxicology in Vitro, 2009, vol. 23, pp. 1007-1013.
Park, E.-J. et al., "Oxidative stress and apoptosis induced by titanium dioxide nanoparticles in cultured BEAS-2B cells", Toxicology Letters, 2008, vol. 180, pp. 222-229.
Premanathan, M. et al., "Selective toxicity of ZnO nanoparticles toward Gram-positive bacteria and cancer cells by apoptosis through lipid peroxidation", Nanomedicine-Nanotechnology Biology and Medicine, 2011, vol. 7, pp. 184-192.
Wu, Y. et al., "The selective growth inhibition of oral cancer by iron core-gold shell nanoparticles through mitochondria-mediated autophagy", Biomaterials, 2011, vol. 32, pp. 4565-4573.
Xue, C. et al., "Nano Titanium Dioxide Induces the Generation of ROS and Potential Damage in HaCaT Cells Under UVA Irradiation", Journal of Nanoscience and Nanotechnology, 2010, vol. 10, pp. 8500-8507.
Zhang, Q.et al., "Autophagy-mediated chemosensitization in cancer cells by fullerene C60 nanocrystal", Autophagy 2009, vol. 5, pp. 1107-1117.
Zhang, Y. et al., "Phototoxicity of Zinc Oxide Nanoparticle Conjugates in Human Ovarian Cancer NIH: OVCAR 3 Cells", Journal of Biomedical Nanotechnology, 2008, vol. 4, pp. 432-438.
Bridot, J. L. et al., "Hybrid Gadolinium Oxide Nanoparticles: Multimodal Contrast Agents for in Vivo Imaging", J Am Chem Soc, 2007, vol. 129, pp. 5076-5084.
Cheon, J. et al., "Synergistically Integrated Nanoparticles as Multimodal Probes for Nanobiotechnology", Accounts of Chemical Research 2008, vol. 41, pp. 1630-1640.
Kim, J. et al., "Multifunctional nanostructured materials for multimodal imaging, and simultaneous imaging and therapy", Chemical Society Reviews, 2009, vol. 38, pp. 372-390.
Mulder, W. et al., "Nanoparticulate assemblies of amphiphiles and diagnostically active materials for multimodality imaging", Accounts of Chemical Research, 2009, vol. 42, pp. 904-914.

* cited by examiner

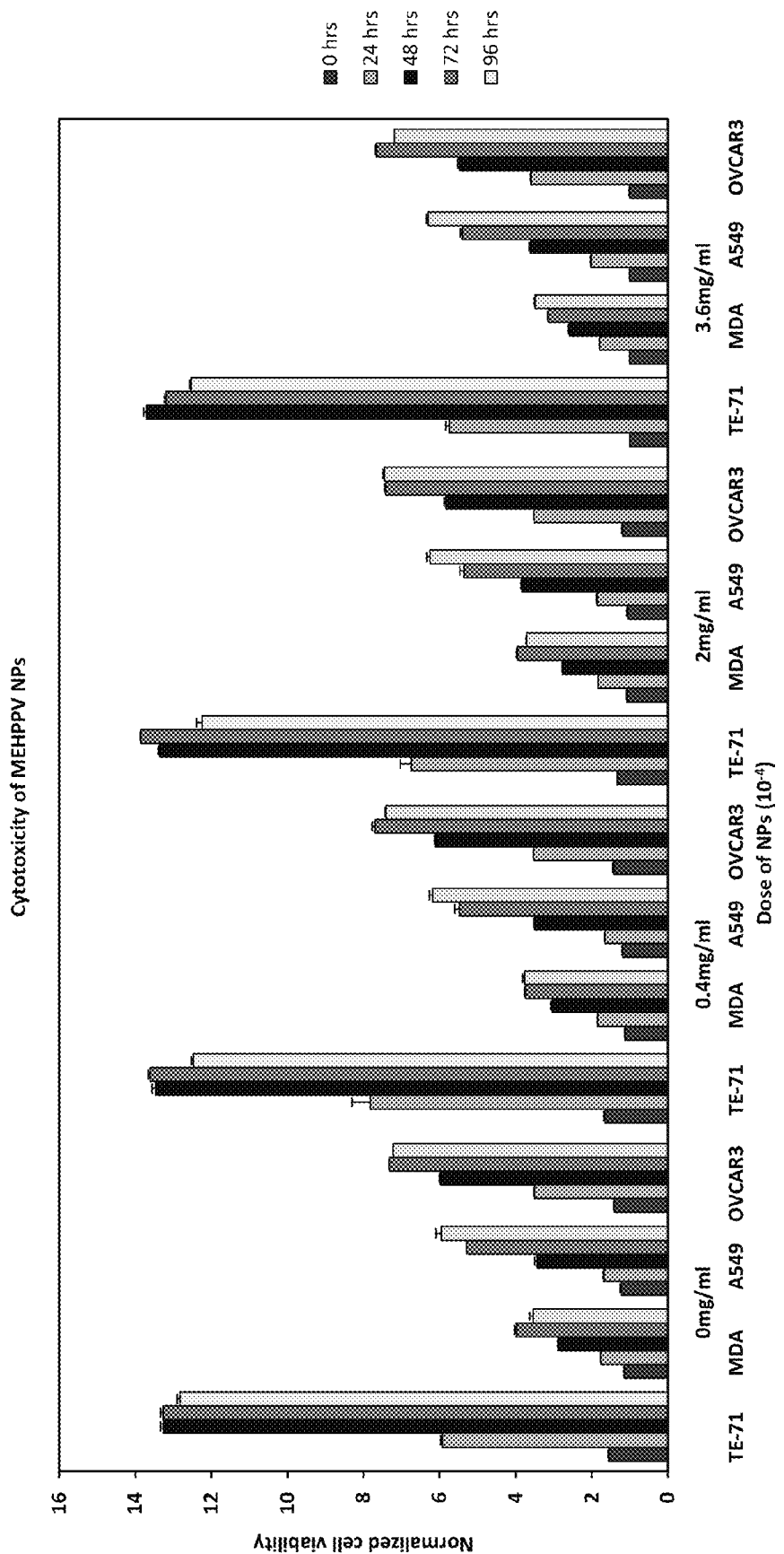
Figure 3.1

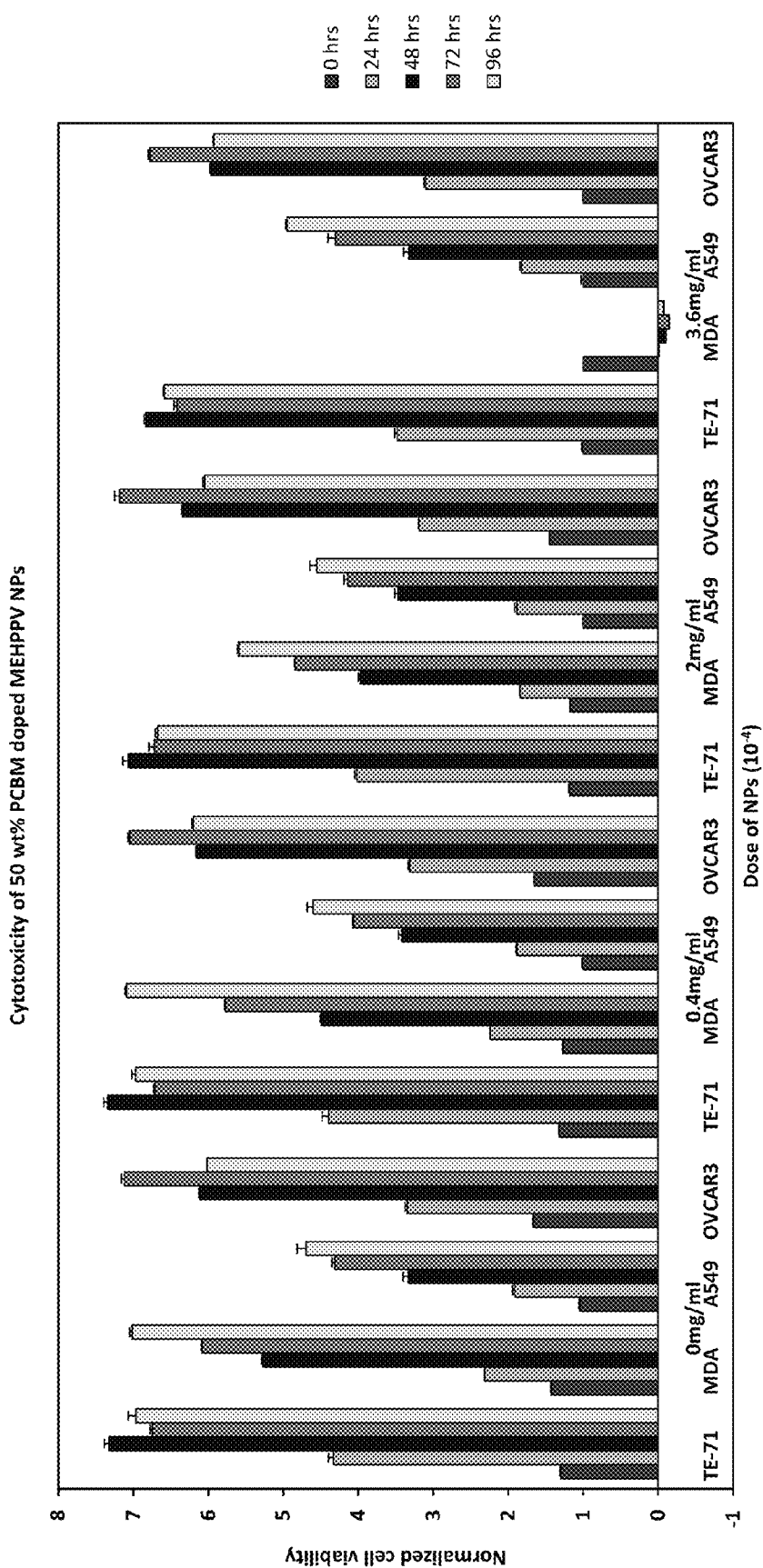
Figure 3.2

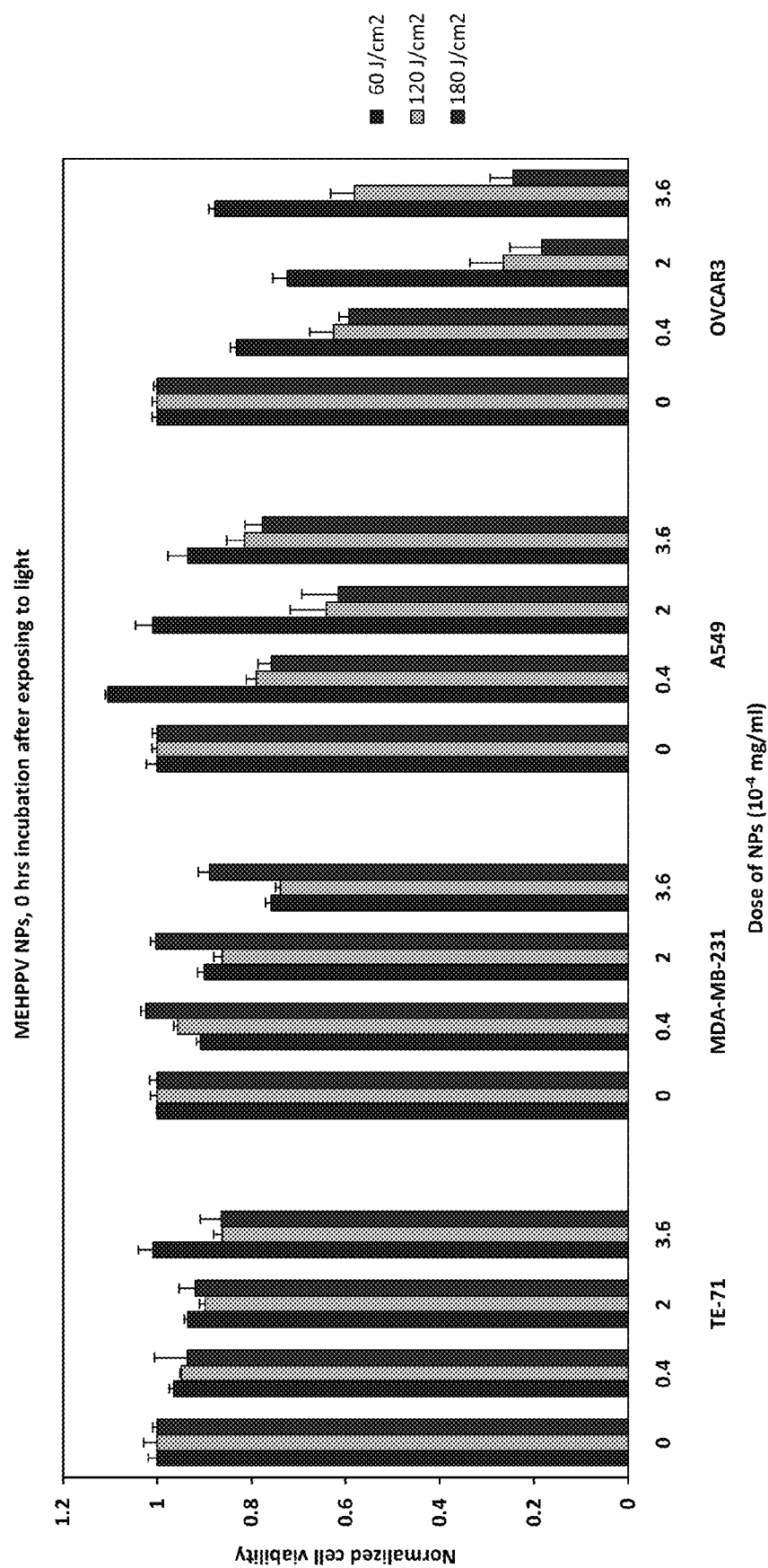
Figure 4.1a

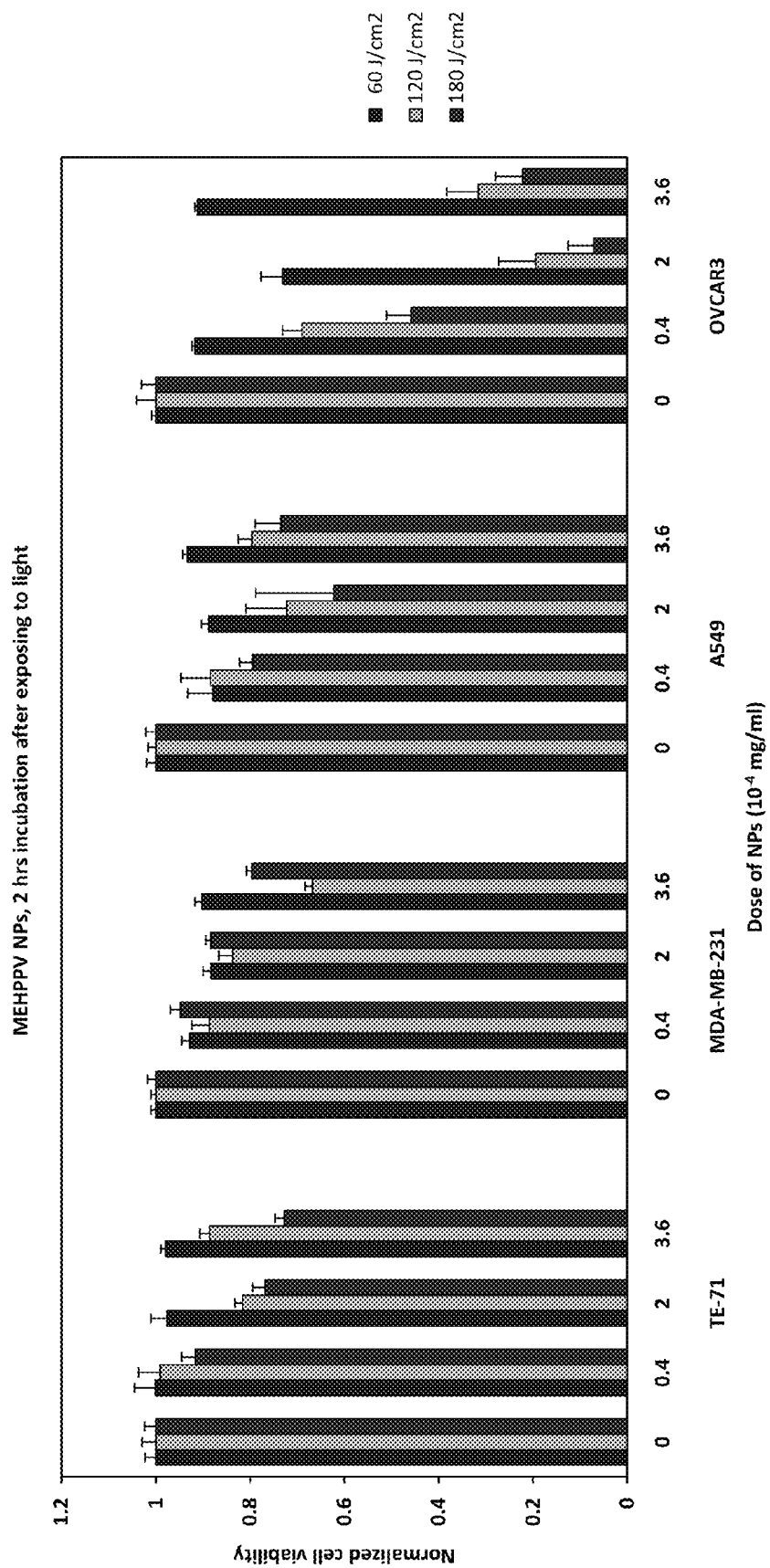
Figure 4.1b

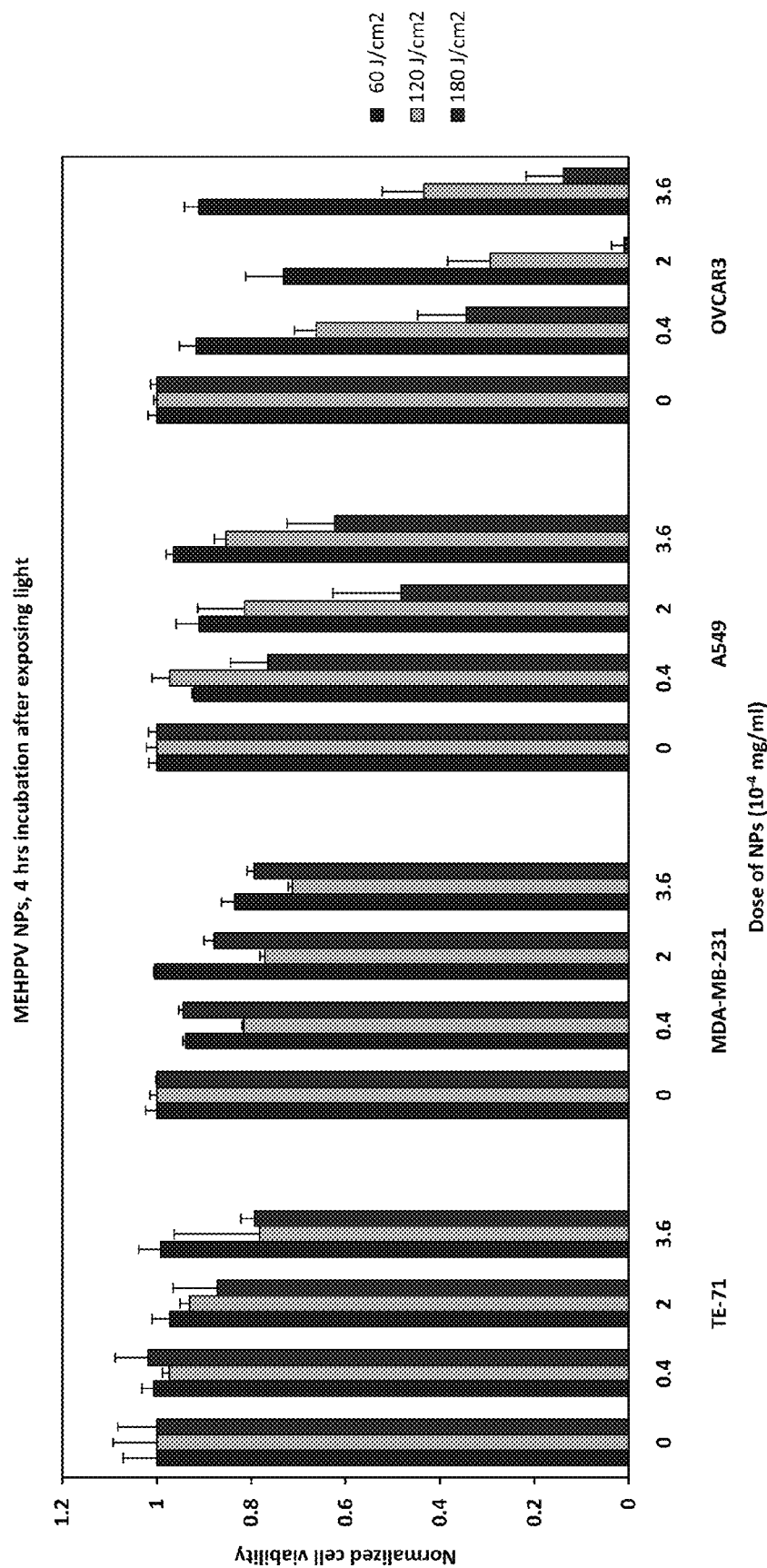
Figure 4.1c

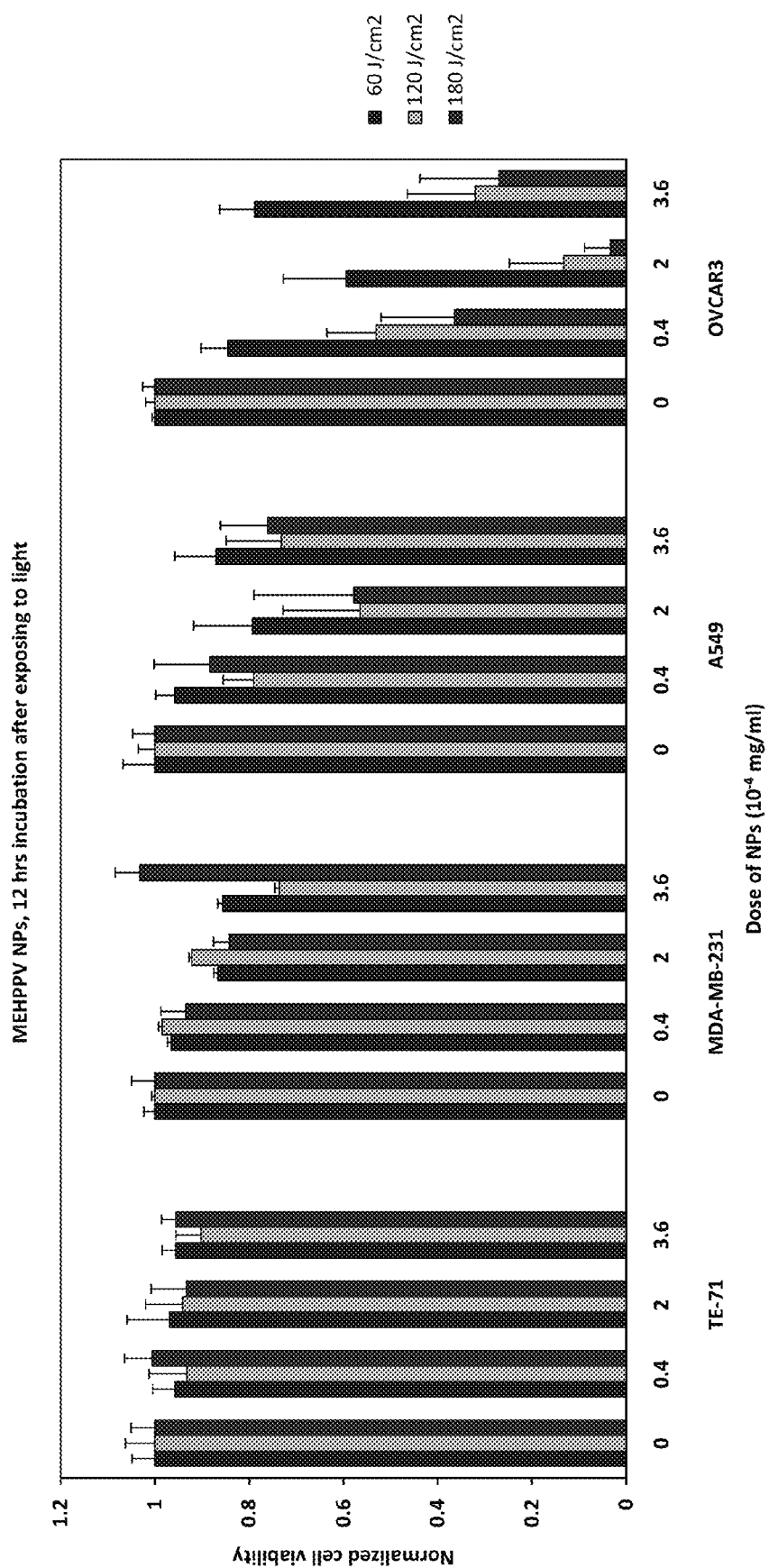
Figure 4.1d

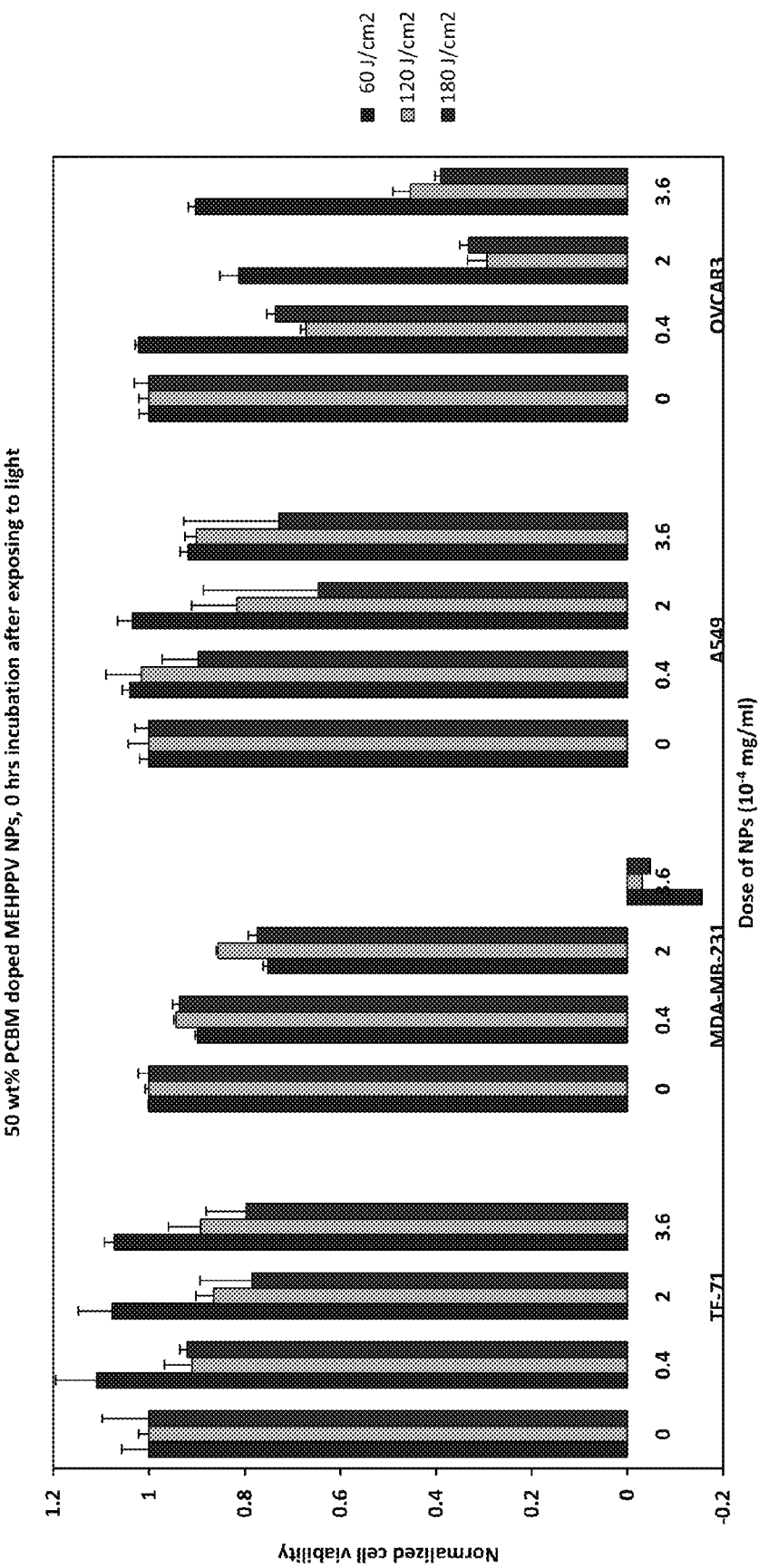
Figure 4.2a

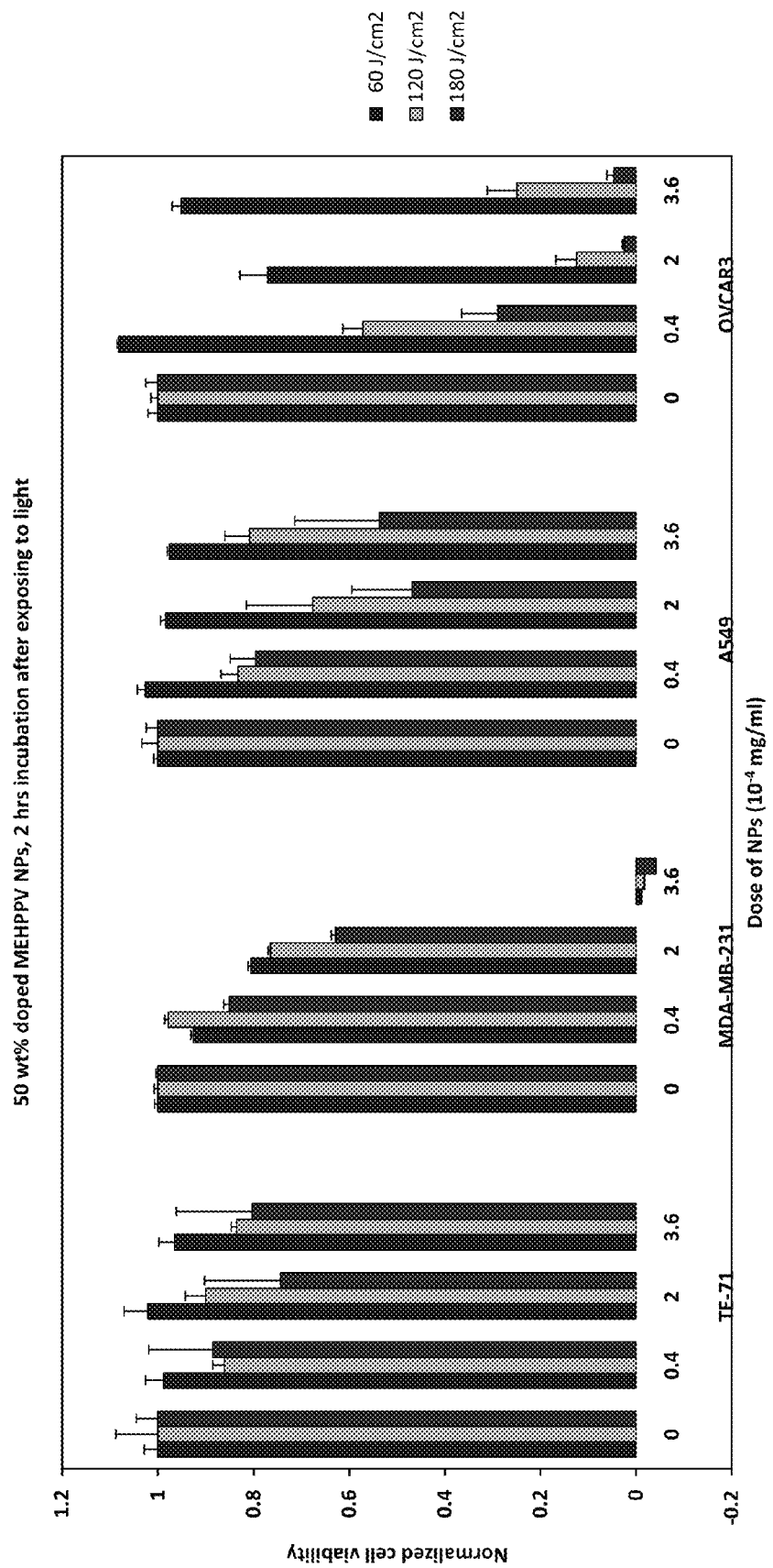
Figure 4.2b

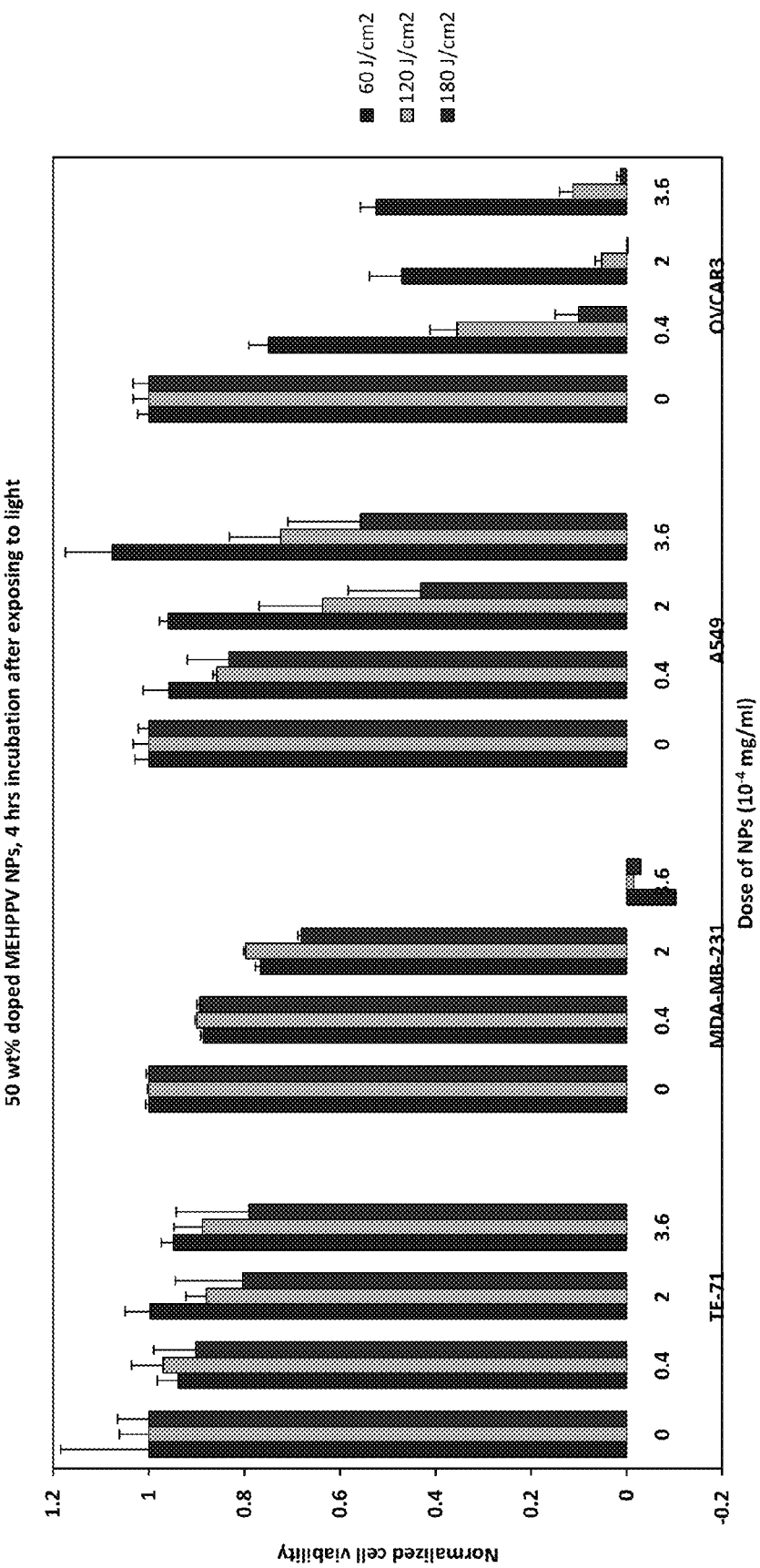
Figure 4.2c

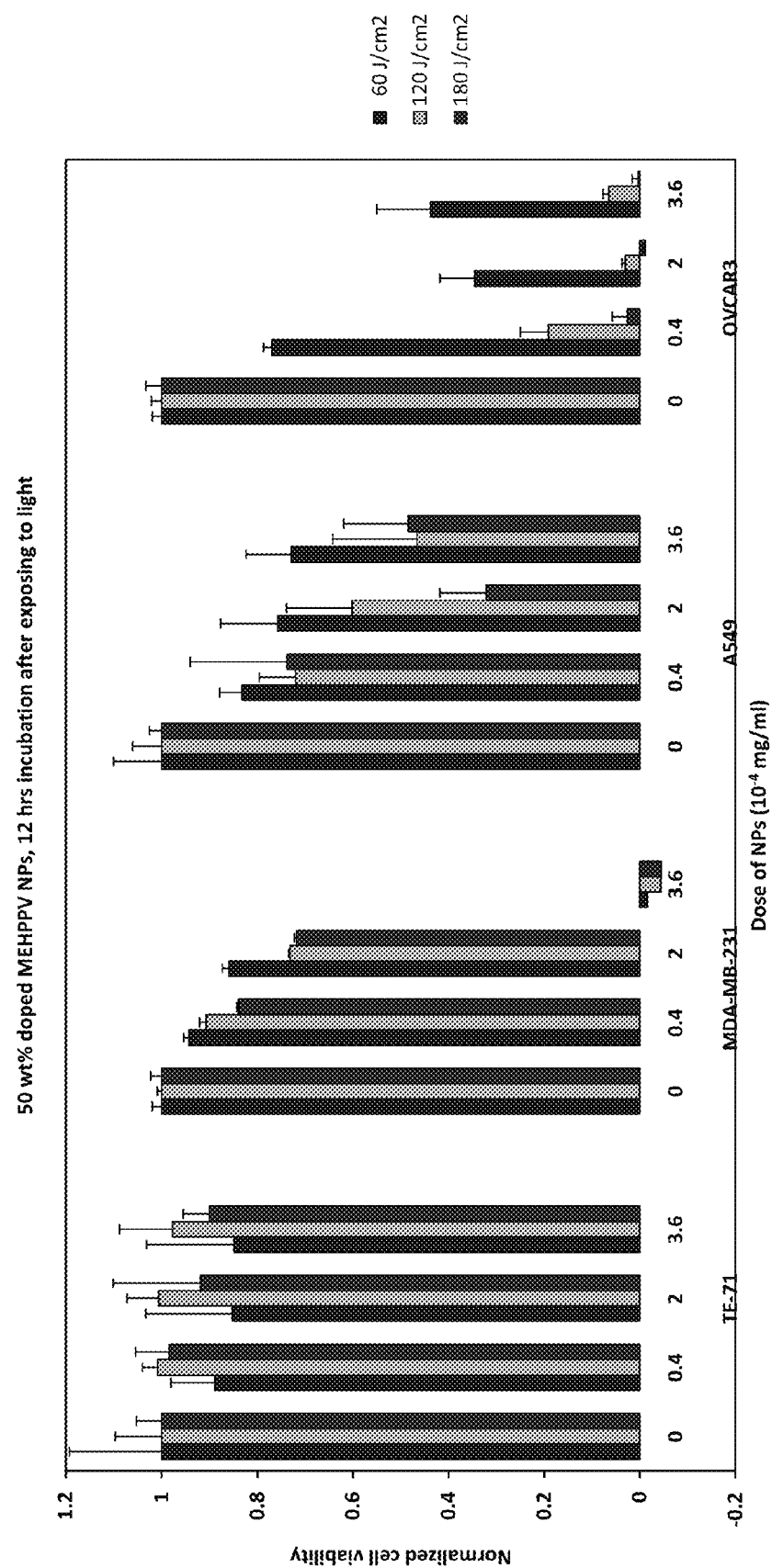
Figure 4.2d

CANCER THERAPY VIA SELECTIVE UPTAKE OF SPECIALIZED NANOPARTICLES IN CANCER CELLS

REFERENCE TO RELATED APPLICATIONS

This application is related to U.S. Provisional application No. 61/544,312 filed Oct. 7, 2011, to which priority is claimed under 35 USC 119. The entirety of this application is incorporated herein by reference.

STATEMENT REGARDING FEDERALLY SPONSORED DEVELOPMENT

The research which forms the basis of this patent disclosure was supported in part by National Science Foundation Career Award No. CBET-0746210. Accordingly, the U.S. Government has certain rights in this invention.

BACKGROUND

Cancer is a disease that covers complex issues including multiple and consistently varying genetic and molecular disorders, while presenting the ability to establish uncontrolled and rapid proliferation. The multitude of factors and forms in which cancer appears introduces major challenges in drug development and treatment. If a drug is successfully designed low efficacy of treatment is often observed due to issues with drug stability, delivery, and efficacy. In addition, drug resistance of cancers is not uncommon. Because of the multifaceted issues associated with cancer, new therapeutic methods need to be designed in a way that accounts for these problems, while facilitating development of products towards commercialization and therapeutics through ease of fabrication, low cost of fabrication, and ease of application in the field. By combining our current understanding of cancer development and function with nanotechnology, novel platforms that address these issues can be envisioned and developed.

SUMMARY

The present disclosure is based on the realization that many types of cancers require elevated ROS for uncontrolled proliferation. Interestingly, this also makes cancer cells more susceptible to ROS induced apoptosis by additional oxidative stress caused by external stimuli. By selectively targeting cancer cells and tumors that exhibit high levels of ROS with nanotechnology based materials that can be externally triggered to initiate elevation of ROS to levels that irreversibly lead to cancer cell death, the development of efficient commercial treatment strategies that differentiate between healthy and normal cells can be developed.

Promising discoveries have been made following the successful design and development of conjugated polymer and composite conjugated polymer-fullerene nanoparticles. Under photoexcitation, these 2 types of nanoparticles can form reactive oxygen species (ROS). The preliminary research on this nanoparticle platform has produced very promising preliminary data that shows that (i) conjugated polymer nanoparticles are taken up abundantly by cancer cells but not by the normal cell line studied, (ii) in dark the nanoparticles are fully biocompatible for all cell lines studied based on viability assays and cell morphology and the fact that cells continue to grow and divide while they contain the nanoparticles, (iii) upon photoactivation the normal cell line shows only minor effects of the treatment, while cancer cell lines show strong effects based on viability assays and cell morphology, (iv) different cancer cell lines also show varying extent of nanoparticle uptake and treatment effectiveness (ovarian cancer shows 100% effectiveness of treatment) and (v) the composite conjugated polymer/fullerene (MEH-PPV/PCBM, 50 wt % PCBM present) are 10-35% more effective when comparing with the conjugated polymer (MEH-PPV only) nanoparticles for the same treatment conditions. These data unmistakably show that the disclosed embodiments are feasible, and moreover, that this treatment approach is highly efficient and can be optimized to distinguish between normal and cancer cells, thus leaving normal cells virtually unaffected. Note that this distinction is based on differences in uptake between normal and cancer cells, as well as the enhanced susceptibility of cancer cells to cell death by oxidative stress compared to normal cells. This is thus a two-pronged approach.

The present disclosure addresses several key hurdles in developing efficient, cost-effective, and targeted treatment of cancer. The nanoparticle technology proposed herein is (i) cheap, (ii) easy to make, (iii) already highly selective to cancer cells without surface functionalization, (iv) biocompatible, (v) highly effective, (vi) and does not suffer from drug resistance issues since the treatment mechanism is not based on use of drugs targeting specific biomolecules or signaling pathways.

Not to be bound or limited to any mechanistic theory, the hypothesis underlying the invention is that organic conjugated polymer and composite conjugated polymer-fullerene nanoparticles can be developed to be a viable commercial nanoparticle platform for cancer treatment that is fully selective to cancer cells, biocompatible, steers clear of healthy cells, circumvents issues with drug resistance, and is highly efficient in treatment success while being cheap and easy to fabricate.

BRIEF DESCRIPTION OF THE DRAWINGS

FIG. 3: Data from MTT assays for thymic epithelial cells (TE-71) and cancer cells (A549 lung cancer, OVCAR-3 ovarian cancer, MDA-MB-231, breast cancer) that were incubated with different doses of conjugated polymer (MEH-PPV, FIG. 3.1) and composite conjugated polymer/fullerene (MEH-PPV/PCBM, 50 wt % PCBM present, FIG. 3.2) nanoparticles. All cell lines proliferate identically to the control, indicating that the polymer nanoparticles do not affect viability and are not inherently cytotoxic.

FIG. 4: Data from MTT viability assays completed on samples for which 3 doses of polymer nanoparticles and 3 doses of light were evaluated in terms of effectiveness towards inducing cancer cell death. Data were compared with controls and the non-cancer cell line TE 71. Incubation with NPs occurred for 0 hrs, 2 hrs, 4 hrs, and 12 hrs for conjugated polymer NPs (FIG. 4.1(*a-d*)) and composite conjugated polymer/fullerene NPs (FIG. 4.2 (*a-d*).

DESCRIPTION

Figure 1:
FIG. 1: Conjugated polymer nanoparticle images acquired with Transmission Electron Microscopy. Nanoparticles were fabricated with (from left to right) approximately 15 nm, 30 nm, 50 nm and 100 nm diameters.

Many innovative and groundbreaking techniques have been developed to treat cancer, ranging from surgical removal of cancer cells to X-ray irradiation to chemotherapy with anticancer agents. However, each of these approaches has its own series of undesirable side effects that are both dangerous and damaging to the overall health of the patient, with the possibility of cancer recurring again. Recent studies on the development of human cancer have identified reactive oxygen species (ROS) as playing a major role in promoting carcinogenesis for a broad variety of cancer cells.[2-5] While many drugs have been investigated to interact with various signaling pathways associated with growth, activity, and proliferation of cancer cells,[4,6-9] one of the signaling pathways that has stood out in terms of understanding the role of ROS in carcinogenesis and cancer proliferation is the PI3K/Akt pathway.[6,10-13] Akt activity in cancer stimulates the consumption of oxygen and leads to increased intracellular ROS by enhancing the oxidative metabolism in mitochondria.[14-17] During the oxidative metabolism in mitochondria single electron reduction of molecular oxygen to superoxide anion occurs in the cell body.[18] These superoxide anions formed in mitochondria are responsible for formation of hydrogen peroxide, which then in presence of iron forms highly reactive hydroxyl radicals. These ROS are more reactive than molecular oxygen. These are essential participants for normal functioning of cells such as in cell signaling and apoptosis. But, if formed in excessive amount ROS can damage the cells oxidatively leading to cell death.[2,3,19-33] Other cell organelles such as the endoplasmic reticulum and the nuclear membrane also have electron transport systems that lead to formation of ROS.[26,32] These ROS are responsible for various diseases like arthritis, cancer and also ageing in body i.e. premature senescence in cells. Interestingly, Hay et al. have shown that while Akt deficiency causes resistance to senescence and ROS mediated apoptosis, the presence of Akt as needed for elevation of ROS in human cancers actually removes that protection, and in fact ROS induced apoptosis in cancer cells becomes facilitated compared to normal cells.[15] In other words, requiring elevated ROS for uncontrolled proliferation potentially also makes cancer cells more susceptible to ROS induced apoptosis by additional oxidative stress caused by external stimuli.[34,35] This double edged sword for human cancer growth and proliferation may in fact open an avenue to selectively target and eliminate cancer cells and tumors that exhibit high levels of ROS. Since cancer cells are expected to be more sensitive to oxidative stress may in fact allow the development of treatment strategies that differentiate the effect of the therapy between healthy and normal cells, i.e. only affecting cancer cells.

Several attempts along this direction have been reported based on inorganic (quantum dots, metal oxide nanoparticles) and metal nanoparticles (gold, silver, iron).[36-46] In these instances intracellular damage and cell death typically occurred due to lipid peroxidation of mitochondria. A concern however is the lack of biocompatibility of these nanomaterials, and in some cases such as quantum dots, cytotoxicity. It is thus unlikely that these approaches will lead to commercial products and therapies. Nevertheless, biophotonics based on novel nanoparticle designs has brought significant advances to sensing, imaging, and therapeutic modalities for biological applications.

The development of nanoparticle based multifunctional and optically active probes, and targeting these bioimaging and biosensing tools to certain cell lines and processes has been a specific point of interest in the research community. These applications are often built around quantum dots or other inorganic nanoparticle materials. Given the promising potential, for instance targeted intracellular delivery that results in increased uptake of cargo (e.g. drug, genes) and increased effectiveness of treatment, or increased effectiveness of therapeutic processes e.g. photodynamic therapy, tremendous research effort has been dedicated to this field of research resulting in many nanomaterial based biosensors and therapeutic drug delivery nanoparticle constructs.[47-50] Nanoparticle based approaches have other key advantages as well: they can be engineered to exhibit specific functionalities, are often intrinsically optically active or paramagnetic, and exhibit higher stability. As just mentioned, there are however several weaknesses that have remained unresolved for the past several years with respect to these developments. Most importantly, not much attention has been given to the cytotoxicity/biocompatibility of such functional biophotonic probes, and not much is known about the fate (e.g. disintegration, aggregation) over longer term. These issues have limited commercialization and application.

Described herein is the application of conjugated polymer and composite conjugated polymer/fullerene nanoparticles with controlled size and surface functionalities in cancer treatment. Earlier studies have been conducted regarding the fabrication and study of the photophysical properties conjugated polymer and composite conjugated polymer nanoparticles.[51-56] One of the objectives of certain inventive embodiments is to achieve a commercial nanoparticle platform for cancer treatment that is fully selective to cancer cells, biocompatible, steers clear of healthy cells, circumvents issues with drug resistance, and is highly efficient in treatment success while being cheap and easy to fabricate.

As discussed above, a promising route is the use of ROS to induce apoptosis in cancer cells. Conjugated polymer and composite conjugated polymer/fullerene nanoparticles have been developed that are photoactivatable nanomaterials and specifically target cancer cells, which in turn lead to highly efficient light activated ROS induced apoptosis of cancer cells. It has been discovered that these nanoparticles were aggressively taken up by OVCAR-3 (ovarian cancer), A549 (lung cancer), and MDA-MB-231 (breast cancer) cell lines even at lowest dose. The experimental data has shown that the photo-activated, targeted therapy is virtually 100% effective for ovarian cancer treatment in-vitro.

In one aspect, provided is a method of treating cancer in a patient in need thereof, the method comprising administering a therapeutically effective regimen, the regimen comprising administering to the patient a therapeutically effective amount of polymer/fullerene nanoparticles, wherein the patient has been diagnosed with cancer. A non-limiting list of cancers to be treated include urothelial carcinoma, cervical cancer, hematologic cancers, such as leukemia and myeloma, thyroid carcinoma, adenoid cystic carcinoma, breast carcinoma, ovarian cancer, prostate cancer, colon cancer, pancreatic cancer, lymphoma, and neuroblastoma leukemia.

In some embodiments, the patient receives a conventional therapy for the treatment of the cancer before, during or after the administration of the therapeutically effective regimen of the invention, the regimen comprising administering to the patient a therapeutically effective amount of polymer/fullerene nanoparticles. A non-limiting list of examples of such a conventional therapy include chemotherapy, radioimmunotherapy, hormonal therapy, small molecule therapy, toxin therapy, prodrug-activating enzyme therapy, biologic therapy, antibody therapy, surgical therapy, including immunotherapy, anti-angiogenic therapy, targeted therapy, epigenetic therapy, demethylation therapy, histone deacetylase inhibitor therapy, differentiation therapy, radiation therapy, and/or any combination thereof.

In another aspect, disclosed is a method of treating cancer in a patient, the method comprising administering to a patient in need thereof polymer/fullerene nanoparticles, wherein the patient is in remission for the cancer. In yet other aspects, the patient has been previously treated with conventional chemotherapeutic agents or had radiation therapy. In yet another aspect, the patient can be treated with the regimens of the invention following, during or prior to the administration of a conventional chemotherapeutic agent or radiation therapy. In yet another aspect, the patient, concurrent with treatment with the regimens of the invention, can be administered a conventional chemotherapeutic agent or can undergo radiation therapy. Further, the cancer can be refractory or multi-drug resistant. In other aspects, the patient can be treated locally with the methods of the invention. For example, a bladder cancer patient could be treated with the invention via local delivery directly into the tumor, or into the bladder. Local treatment with the invention may also be administered in combination, before, or after other local treatments as well (e.g. BCG therapy).

In yet another aspect, provided is a method for preventing a recurrence of cancer in a patient in remission, the method comprising administering to a patient in need thereof a prophylactically effective regimen, the regimen comprising administering to polymer/fullerene nanoparticles. In another aspect, the invention provides a method for preventing a recurrence of cancer in a patient that has already undergone conventional cancer treatment, the method comprising administering to a patient in need thereof a prophylactically effective regimen, the regimen comprising administering to the patient polymer/fullerene nanoparticles.

In another aspect, provided is a method of treating a solid tumor in a patient, the method comprising administering to a patient in need thereof a therapeutically effective regimen, the regimen comprising administering to the patient with polymer/fullerene nanoparticles wherein the patient has been diagnosed with a solid tumor, and wherein the patient has undergone primary therapy to reduce the bulk of the tumor. In some embodiments, the primary therapy is, for example, chemotherapy, radioimmunotherapy, hormonal therapy, small molecule therapy, biologic therapy, toxin therapy, prodrug-activating enzyme therapy, antibody therapy, surgical therapy, immunotherapy, anti-angiogenic therapy, targeted therapy, differentiation therapy, epigenetic therapy, demethylation therapy, histone deacetylase inhibitor therapy, radiation therapy, or any combination thereof.

In particular embodiments of this aspect, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiform, astrocytoma, medulloblastoma, craniopharyngioma, ependymoma, pinealoma, hemangioblastoma, acoustic neuroma, oligodendroglioma, meningioma, skin cancer, melanoma, neuroblastoma, or retinoblastoma.

According to another embodiment, the disclosure is directed to polymer/fullerene nanoparticles that have selective uptake into cancer cells, and which, upon being taken into the cancer cells induce apoptosis. Induction of apoptosis can be controlled by activation of the nanoparticles. Activation can occur such as by photoactivation, or other means.

Examples

Nanoparticle Fabrication and Characterization

Figure 6:
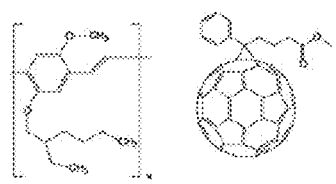
FIG. 6: Chemical structure of conjugated polymer MEH-PPV (left, poly[2-methoxy-5-(2-ethylhexyl-oxy)-p-phenylenevinylene]) that comprises the nanoparticle core. In the case of composite nanoparticles the fullerene (right, Methoxycarbonylpropyl-1-phenyl-[6.6]C61) is also present

There have been publications regarding extending the reprecipitation method towards the development of nanoparticles of the conjugated polymer poly[2-methoxy-5-(2-ethylhexyl-oxy)-p-phenylenevinylene] (MEH-PPV), as well as composite particles of MEH-PPV and the fullerene 1-(3-Methoxycarbonylpropyl)-1-phenyl-[6.6]$C_{61}$ (PCBM).[54] The reprecipitation method is a simple solution processing technique in which a solution of organic material in good solvent is injected into a very poor solvent for the organic material. Upon injection a stable suspension of nanoparticles is formed due to hydrophobic aggregation of the compounds when entering the water phase. Zeta potential measurements for these conjugated polymer (MEH-PPV) and composite conjugated polymer/fullerene (MEH-PPV/PCBM, 50 wt % PCBM present) nanoparticles reveal a slightly negative charge (−12.4 mV and −9.7 mV, respectively). By varying preparation parameters, the preliminary control over the nanoparticle size is achieved, see FIG. 1. Control of size and size distribution is one of the needs for commercialization that is in this disclosure, since these will affect cellular uptake and nanoparticle clearance from the body. Tenery, D.; Gesquiere, A. J. *Chemphyschem* 2009, 10, 2449 and Tenery, D.; Worden, J. G.; Hu, Z. J.; Gesquiere, A. J. *Journal of Luminescence* 2009, 129, 423 are cited by reference for information regarding nanoparticles and alternative embodiments of nanoparticles that may be used in accordance with the teachings herein. FIG. 6 shows the chemical structure of conjugated polymer MEH-PPV.

Studies on Nanoparticle Uptake

Figure 2:
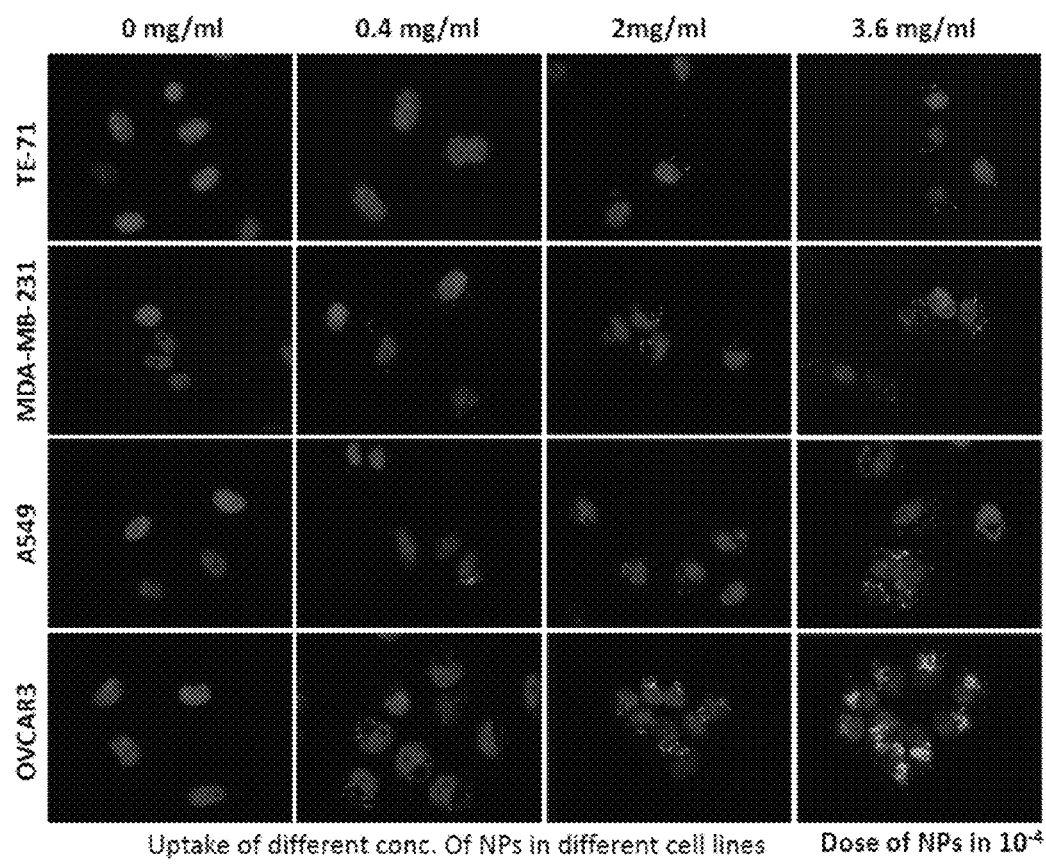
FIG. 2: Confocal fluorescence images of different cell lines (OVCAR3, A549, MDA-MB-231 and TE-71 cells) incubated with conjugated polymer (MEH-PPV) nanoparticles harvested from 96 well plates (in preparation for MTT viability assays). The cells were trypsinized, plated, fixed, and stained with DAPI before imaging. Differences in nanoparticle uptake are clearly visible. Similar results were obtained with the composite conjugated polymer/fullerene (MEH-PPV/PCBM, 50 wt % PCBM present) nanoparticles (data not shown).

Thymic epithelial cells (TE-71) and cancer cells (A549 lung cancer, OVCAR-3 ovarian cancer, MDA-MB-231, breast cancer) were incubated with different doses of the 30 nm nanoparticles (which have shown the best results in-vitro, thus were used throughout the studies) for 1 hr, 2 hr, 5 hr, 12, 24, 48, 72, and 96 hrs. The data shown in FIG. 2 are for 24 hrs incubation. Surprising differences in cellular uptake were observed given that the nanoparticles do not posses functionality that specifically targets them to certain cell lines. The normal cell line TE 71 takes up only limited amounts of nanoparticles at the higher doses of nanoparticles that were considered. Conversely, the OVCAR-3 ovarian cancer, MDA-MB-231 breast cancer, and A549 lung cancer cell lines aggressively take up nanoparticles even at the lowest dose of nanoparticles. There is however a distinguishable difference amongst the cancer cell lines as well, OVCAR-3 takes up much more nanoparticles than A549. At the highest dose the difference becomes harder to observe due to the abundance of nanoparticles.

Evaluation of Biocompatibility

Cytotoxicity of the polymer nanoparticles was evaluated by MTT assays. Standard MTT assays were completed on samples in 96 well plates that were incubated 0, 24, 48, 72, and 96 hours for the different doses that were studied. The data clearly show that cells proliferate identically to the control, indicating that the polymer nanoparticles do not affect viability and are not inherently cytotoxic. This finding applies to both the conjugated polymer (MEH-PPV, see FIG. 3.1) and composite conjugated polymer/fullerene (MEH-PPV/PCBM, 50 wt % PCBM present, see FIG. 3.2) nanoparticles, and is distinctly different from pure C60 materials.[60]

Evaluation of Treatment Scheme

The hypothesis that these all-organic polymer nanoparticles can be photoactivated to induce oxidative stress and cell death selectively for cancer cell lines through ROS was tested by incubating thymic epithelial cells (TE-71) and cancer cells (A549 lung cancer, OVCAR-3 ovarian cancer, MDA-MB-231 breast cancer) with the nanoparticles as discussed above. Incubation with nanoparticles took place in 96 well plates for 24 hours. The light dose (mercury lamp, UV filtered by 400 nm longpass filter) was varied in 3 experiments (60, 120, and 180 J/cm$^2$), and in each experiment 3 doses of nanoparticles (0.4, 2, and 3.6×10$^{-4}$ mg/ml) were tested together with a control (no particles). After exposure the samples were again incubated (dark) for 0, 2, 4, and 12 hours. Then standard MTT assays were completed to determine cell viability and thus treatment effectiveness. It was surmised that the addition of fullerene (PCBM) that results in composite conjugated polymer/fullerene (MEH-PPV/PCBM, 50 wt % PCBM present) nanoparticles would lead to enhanced generation of ROS under light exposure compared to conjugated polymer (MEH-PPV only) nanoparticles due to the additional charge transfer mechanism that produces radicals on polymer and fullerene in the composite nanoparticles. Specifically, in the case of the conjugated polymer nanoparticles the ROS mechanism occurs by intersystem crossing after photoexcitation followed by triplet-triplet energy transfer to molecular oxygen, which then converts to singlet oxygen.

For the composite nanoparticles, an additional mechanism is available that involves photoinduced charge transfer from the conjugated polymer to the fullerene doped in the nanoparticles, which leads to formation of free radicals. The results are shown for the conjugated polymer (MEH-PPV, see FIG. 4.1(a-d)) and composite conjugated polymer/fullerene (MEH-PPV/PCBM, 50 wt % PCBM present, see FIG. 4.2) nanoparticles, specifically for the sample set that was incubated for 4 hours after light exposure (0, 2, and 12 hours not shown). These data show that (i) the photoactivated treatment is virtually 100% effective for ovarian cancer at the 180 J/cm$^2$ light dose, (ii) TE 71 (normal) cells show at most 20% reduction in viability, and mostly within experimental error, (iii) A549 shows intermediate behavior between normal and ovarian cancer cells, (iv) the treatment plateaus for the 2×10$^{-4}$ mg/ml for both cancer cell lines, (v) the 180 J/cm$^2$ light dose gives an upper limit for required light dose to observe 100% effective treatment of ovarian cancer cells in-vitro, (vi) the composite conjugated polymer/fullerene (MEH-PPV/PCBM, 50 wt % PCBM present) are 10-35% more effective when comparing with the conjugated polymer (MEH-PPV only) nanoparticles for the same conditions.

Figure 5:
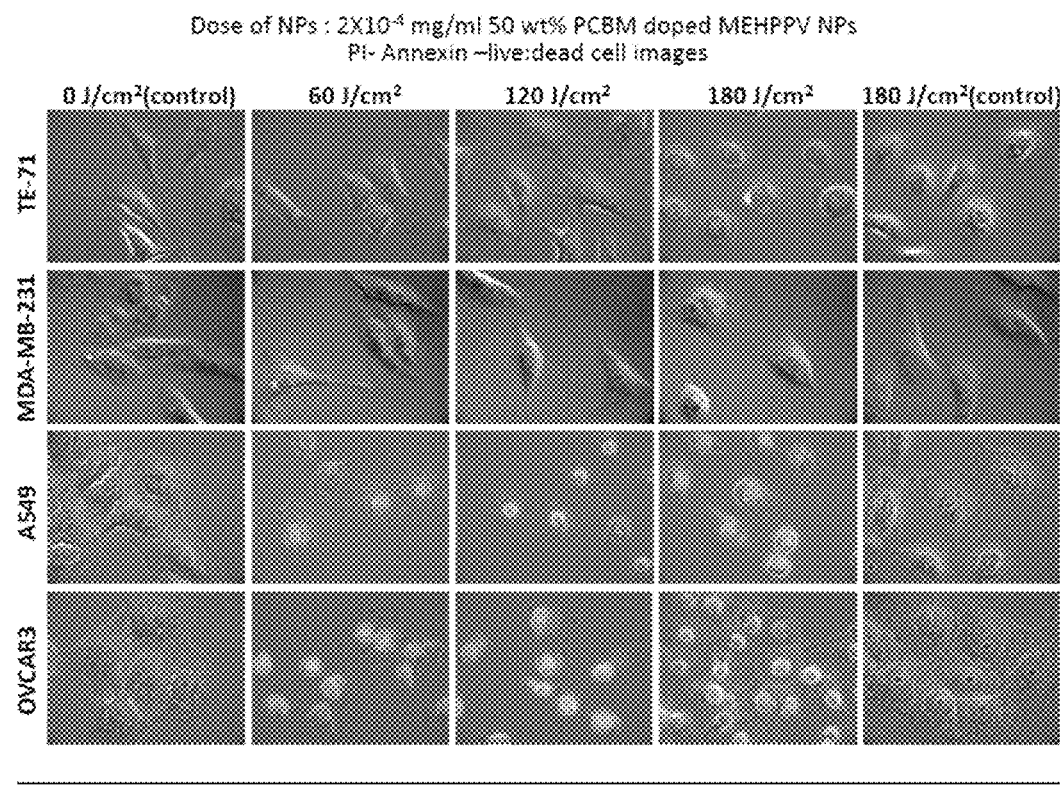
FIG. 5: In-vitro imaging on A549, MDA, OVCAR-3, and TE 71 cell lines stained with PI and annexin reveals changes in morphology and cell death for the cancer cell lines at all light doses studied. At the lowest dose the effects are moderate, while at the higher light doses observations are unambiguous. The TE 71 (non-cancer) cell line only shows changes in morphology at the highest light dose used in this study. Most cells still appear viable however based on the absence of PI or annexin fluorescence in the majority of cells. Cells incubated with nanoparticles but kept in dark, and cells without particles dosed with 180 J/cm2 of light appear viable based on morphology and absence of PI or annexin fluorescence. These observations correspond well with the MTT assays on effectiveness of treatment, absence of nanoparticle cytotoxicity in dark, and differences in extent of nanoparticle uptake by the cell lines. Polymer nanoparticle dose used in this study was 2×10-4 mg/ml.

The data for MTT assays on cells taken 0, 2, and 12 hours incubation after light exposure (not shown) indicate that (i) immediately after administering light doses cancer cell lines show reduced viability, (ii) TE 71 (normal) cells show no further change in cell viability after 2, 4, and 12 hours incubation compared to data obtained immediately after administering light doses (0 hrs incubation followed by MTT assay), and (iii) 12 hours incubation does not show better results than waiting 4 hours before completing MTT assays after administering light doses These observations were further confirmed by fluorescence (live/dead staining) and phase imaging on cells of the four studied cell lines plated in petri dishes and dosed with nanoparticles and light under identical conditions as the samples in 96 well plates. In addition, these samples were stained with PI (Propidium Iodide) and annexin to observe necrosis and apoptosis, respectively. These data, as shown in FIG. 5 show that treatment of OVCAR-3 (which takes up the most nanoparticles) is the most effective. At the medium light dosage apoptosis and necrosis is observed, while at the higher light dosage only necrosis is observed. Cell morphology clearly indicates treatment induced death. In dark and under treatment of the highest light dose in the absence of nanoparticles there is no observable cell damage. The PI and annexin stains give a negative result and the cell morphology appears pristine. Similar observations are made for A549, but less dramatic due to the lower uptake of nanoparticles by that cell line. The TE 71 cell line is not affected by treatment except at the highest light dosage. The PI and annexin stains give a negative result and the cell morphology appears pristine in all other cases. Further improvement of targeting of the nanoparticles to cancers is one of the needs that will be addressed in this proposal. Taken all together, these photoactivated polymer nanoparticle treatment data show that this is a highly effective treatment approach for cancer cell lines that shows very promising results in-vitro. Specifically, the treatment is based on biocompatible all-organic nanoparticles that result in a photoactivatable cancer cell treatment scheme that is benign to non-cancer cells, highly effective towards cancer cells, works under relatively low light conditions for reasonable short exposure times (due to the high absorption cross-section of the polymer nanoparticles) thus avoiding phototoxicity, is fully effective in 1 treatment for ovarian cancer cells and about 50% effective for A549 cancer cells 4 hours after treatment was initiated, and already shows specificity to cancers without modification of bare nanoparticles. In-vitro a nanoparticle dose of 2×10$^4$ mg/ml (for 5,000 cells) together with a light dose of 180 mJ/cm$^2$ is already sufficient to observe these results 4 hours after treatment. To give a practical example, the 180 mJ/cm$^2$ light dose corresponds with exposure to full direct sunlight (measured at sea level, minus UV portion of spectrum which we filtered out) experienced for 30 minutes, cytoxicity issues are thus expected to be minimal. Differences between the effectiveness of treatment between the OVCAR-3, MDA, and A549 cancer cell lines observed in-vitro can be attributed mainly to the difference in nanoparticle uptake between these two cell lines, as shown above.

Optimized Design of all-Organic Polymer Nanoparticles to Facilitate Fabrication of Samples with Controlled Size on Large Scale As described in the Examples above, nanoparticle fabrication so far has proceeded by the reprecipitation method. While this is a very quick and easy method to produce conjugated polymer nanoparticles in the lab, there are several issues that make this method less than ideal for commercialization of the proposed nanoparticle platform for treatment of cancer tumors:

1. The method produces small quantities of material and is difficult to scale up
2. The nanoparticles cannot easily be functionalized further Thus, while the reprecipitation method is ideal for lab settings, these issues need to be addressed in order to advance to commercialization.

Figure 7:
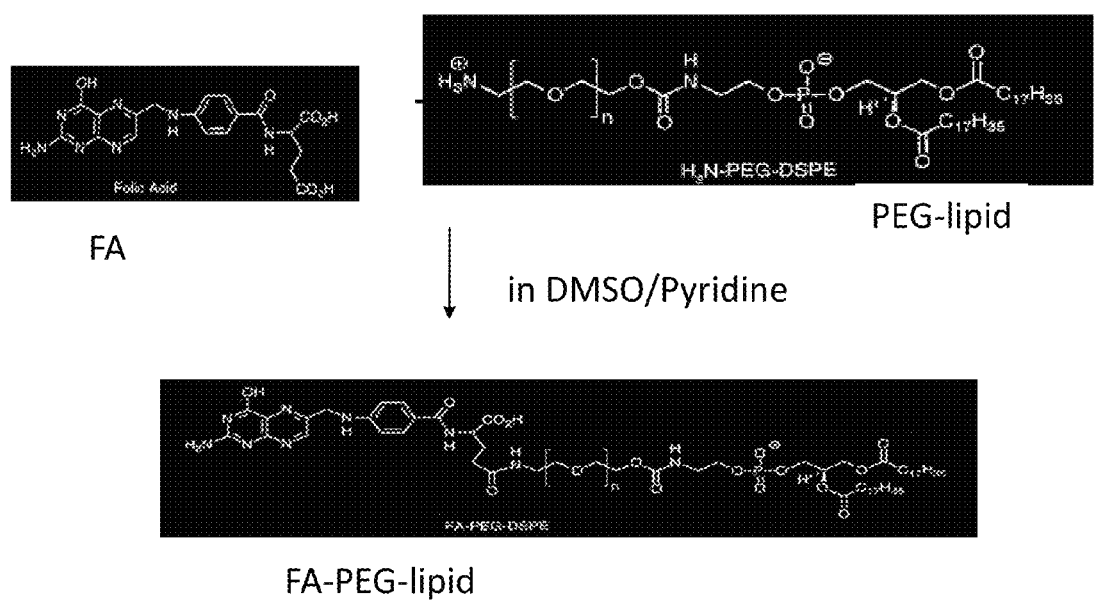
FIG. 7: Scheme of FA-PEG-lipid synthesis

Described here is a nanoparticle fabrication method based on nanoemulsions (see FIGS. 6 and 7). The method is a modification of a recently reported method for conjugated polymer nanoparticle synthesis.[61] Nanoemulsions are defined as a mixture of two immiscible phases, in which the dispersed phase of one substance stabilized by surfactants is suspended in the continuous phase of the other as nanoscale colloids. This approach offers a number of benefits including a narrow particle size distribution and a high production yield. The resulting nanoparticles will be coated with a PEG-lipid layer that has reactive groups for further functionalization. In addition, PEG-lipid layers on nanoparticle surfaces have been shown to enhance buffer and plasma stability, enhanced circulation times in-vivo, and low toxicity. Furthermore, PEG has already been extensively used in clinical applications, which is an advantage in moving towards commercialization and FDA approval.

Figure 8:
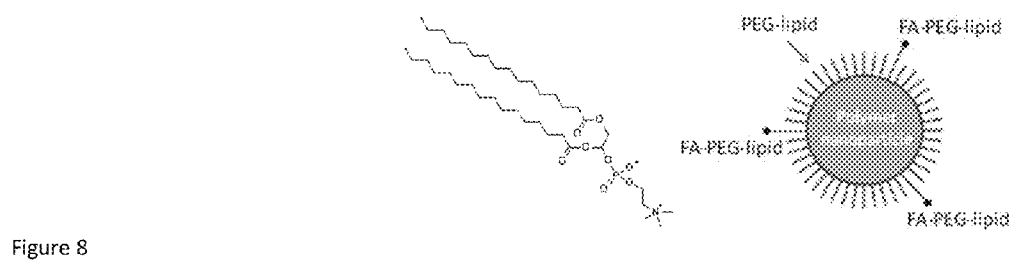
FIG. 8: Left: Structure of phospholipid that will be used, DPPC (Dipalmitoylphosphatidylcholine). Right: Cartoon of FA-conjugated PEG-lipid encapsulated conjugated polymer nanoparticle.

According to another embodiment, PEG-lipid encapsulated all-organic conjugated polymer nanoparticles are fabricated as follows. First, folic acid-poly(ethylene glycol)-distearoyl-phosphatidylethanolamine (FA-PEG-lipid) will be synthesized by the carbodiimide-mediated coupling of FA to $H_2N$-PEG-lipid, in which amino-PEG-lipid and pyridine will be added to an FA and dimethyl sulfoxide (DMSO) solution, followed by dicyclohexylcarbodiimide. The reaction will be carried at room temperature for several hours and then pyridine will be removed by rotary evaporation. The resultant FA-PEG-lipids will be purified with silica gel column and then characterized with NMR, UV-vis analysis, and mass spectra. The choice of FA as a functionalizing group is obvious in that it is well known that the receptor for the folic acid is over expressed in a number of human tumors. Because of the high affinity of folic acid for the folate receptors present at the surface of these cancers, folic acid (FA)-lipid micelles can enhance the selective internalization into cancer cells in the presence of normal cells compared to the bare conjugated polymer nanoparticles (which already show a great degree of selectivity, see preliminary data). Second, the synthesis of polymer nanoparticles will be carried out with nanoemulsion technology in folate-targeted lipid micelles, see FIG. 8. The conjugated polymer (together with fullerene in the case of the composite conjugated polymer-fullerene nanoparticles), FA-PEG-lipid and PEG-lipid will be completely dissolved in dichloromethane (DCM), and will then be added to water under rapid stirring and excitation with a conical tip sonicator. The result will be the formation of micellar droplets in the water phase that contain DCM. The DCM will evaporate from the micelles, leaving nanoparticles suspended in water that are encapsulated with FA-PEG-lipid and PEG-lipid driven by hydrophobic forces. This is a 1 step FA-conjugated PEG-lipid encapsulated conjugated polymer nanoparticle fabrication process that is suitable for scale up during commercialization.

According to a further embodiment, the size of the FA-PEG-lipid/PEG-lipid folate-lipid encapsulated polymer nanoparticles is changed by altering the energy of sonication provided by the conical tip sonicator and the sonication time. The number of FA groups present on the micelle surface will be controlled by varying the mixing ratio of the FA-PEG-lipid and the PEG-lipid in solution. The size and its distribution of the resulting folate-targeted micelle encapsulated polymer nanoparticles will be characterized by dynamic light scattering (DLS, hydrodynamic radius) and Transmission Electron Microscopy (TEM, radius of polymer core). Size differences between the methods will be mainly due to the observation of the lipid encapsulation layer by DLS, which will not be noticeable in TEM. Charge of the nanoparticles will be determined by measuring the zeta potential of nanoparticles. It will be measured by suspending the nanoparticles in Hepes buffer (ionic strength 40 mM, pH 7.4). The Smoluchowski equation will be used in the experiment.

The revised fabrication process described above provides several advantages: nanoparticles can be fabricated at large scale, afford excellent control of size and its distribution (needed for field deployment), enhances stability and circulation in the blood stream, allow for surface functionalization, and is based on FDA approved encapsulation materials.

Characterize Targeting of all-Organic Polymer Nanoparticles to Cancer Cells In-Vitro and Evaluate Biocompatibility Uptake of the surface functionalized all-organic polymer nanoparticles by normal and cancer cells in-vitro is evaluated by confocal fluorescence microscopy. Since the conjugated polymer nanoparticles are inherently fluorescent no further tagging with fluorescence labels is necessary.

The selectivity of cellular uptake is studied for different cell lines that are incubated with the proposed FA-functionalized all-organic polymer nanoparticles. Normal thymic epithelial cells (TE-71) and cancer cells (A549 lung cancer, OVCAR-3 ovarian cancer, and MDA-MB-231 breast cancer are treated with nanoparticles and incubated for 1 hr, 2 hr, 5 hr, 12 and 24 hr. Experiments are carried out in small petri dishes in 5% FBS at 37° C. and 5% $CO_2$ in humid conditions. The cells are fixed after the specific time periods by using paraformaldehyde and are suspended in PBS for imaging. To image the fixed cells spinning disc laser scanning confocal microscopy is used by using 488 nm line as excitation source for nanoparticle imaging. The emission of the nanoparticles peaks at 595 nm. Localization of the nanoparticles in the cells is monitored by staining the nucleus with DAPI (excitation 350 nm, emission 500 nm) and the cell membrane with is stained with CellMask Deep Red plasma membrane stain (Invitrogen, excitation 633 nm, emission 666 nm), followed by collecting confocal slices of the samples. Staining is conducted according to established protocols. It has been demonstrated by preliminary studies that the bare nanoparticles already show strongly selective uptake in cancer cells compared to normal cells. With surface functionalization of the nanoparticles it is expected to improve further on these promising results.

The biocompatibility of the surface functionalized all-organic polymer nanoparticles prepared as described above is evaluated. MTT assays are completed "in dark" i.e. on cells that were incubated with the nanoparticles while remaining stored in the incubator (implying no purposeful exposure to significant doses of light). Normal and cancer cells are treated in 96 well plates with nanoparticles and incubated for 1 hr, 2 hr, 5 hr, 12 and 24 hr. To complete the MTT assay, media from well plates treated with nanoparticles are removed and are replaced with serum free, drug-free media. MTT are added to each well and cells are incubated for an hour. After this, absorbance is measured at 595 nm using a microplate reader. As a control, cells not treated with nanoparticles are also tested for viability.

The functionality of the nanoparticles is also evaluated in terms of treatment in-vitro after modification of the synthesis method and surface functionalization (described above) Cells are treated with nanoparticles and incubated as stated above. Then the proper dosage of light is given to cells, which has been established through preliminary experiments (see examples above), and cells are incubated for 0, 2, 4, and 12 hours after illumination before the MTT assay is performed. The MTT assay will quantify the effectiveness of treatment for the different cell lines with respect to the control. In addition, cell morphology is evaluated by light microscopy.

Characterize In-Vivo Applications of Optimized all-Organic Polymer Nanoparticles Towards Treatment of Cancer Tumors To successfully move the surface functionalized all-organic polymer nanoparticles from in-vitro studies to in-vivo application and towards commercialization the following considerations are made: First, the optimum dosage necessary for enhanced bioavailability and delivery to tumor sites needs to be assessed. The delivery to tumor sites are monitored by fluorescence imaging using a Kodak in-vivo system. Second, the efficacy of the surface functionalized all-organic polymer nanoparticles for tumor treatment is evaluated in conjunction with optimizing the administered light dose for photoactivation of treatment. Finally, clearance of the nanoparticles from the animal body is evaluated.

Dosing assessment is studied and surface functionalized all-organic polymer nanoparticle accumulation is evaluated in tumor sites. In these studies, mice bearing subcutaneous tumors of A549 lung cancer, OVCAR-3 ovarian cancer, and MDA-MB-231 breast cancer are dosed according to the following schedule: (i) 3 doses (i.v.), given in 2-day intervals i.e. on days 1, 3, and 5, and at 3, 9, 24, and 36 h after each dosing, anesthetize mice and image using a Kodak In Vivo Imaging System; and ii) 3 doses, given in 4-day intervals i.e. on days 1, 5, and 9, and at 3, 9, 24, 48, 72, and 84 h after each dosing, anesthetize mice and image using a Kodak In Vivo Imaging System. In-vivo intra-tumor localization, tumor vasculature, and duration of intra-tumor availability is monitored.

Since the conjugated polymer nanoparticles are inherently fluorescent no further tagging with fluorescence labels may be necessary. Preliminary nanoparticle fluorescence imaging results that show extremely high brightness of these nanoparticles compared to e.g. quantum dots, even in the presence of fullerene in the nanoparticle core. This is due to the presence of multiple emitting polymer molecules in the nanoparticle core. Using the emissive properties of the conjugated polymer nanoparticles, the degree of fluorescence signal intensity accumulation and decay between the two dosing schedules is determined. Animals are then sacrificed at the end of the study and tumor tissue extracted and imaged, weighed, and then sectioned and imaged. These studies will provide data on tumor vasculature, and will guide in the dosing levels to be used in efficacy studies. Two dosing schedules for two types of polymer nanoparticles (conjugated polymer and composite conjugated polymer/fullerene) applied to three tumor models repeated in triplicate will be used, thus 4 conditions×3 replicates×3 tumor models=36 mice will be used for fluorescence-based imaging.

Antitumor efficacy of the polymer nanoparticles is evaluated while concurrently determining the optimal light dosage in-vivo. The surface functionalized all-organic polymer nanoparticles is evaluated at the 2 dosing schedules discussed above i.e. (i) every 2 days, and (ii) every 4 days, and for both types of polymer nanoparticles (conjugated polymer and composite conjugated polymer/fullerene), by testing three light doses for photoactivation, and a control specimen (0 dose of polymer nanoparticles) i.e. 5 conditions per tumor model (5 conditions×3 light doses×3 replicates×3 tumor models=135 tumor-bearing mice). Subcutaneous xenografts of human breast, lung, and ovarian cancers is developed by injecting cancer cells ($5 \times 10^6$ in 100 µL medium) into the right and left flanks of mice.[62,63] Mice are monitored daily for tumor formation, sizes, and numbers by caliper measurements. One to three weeks after implantation, tumors will be staged and treatments initiated. Healthy tumor-bearing mice (with 50 mm$^3$ size tumors) are randomized into test groups, and treated by i.v. injection through the tail vein for 10 weeks.[62,63] During the study, animals will be monitored and examined daily for signs of gross toxicity. Tissue is to be examined should such toxicity events occur. The light dosage to be administered during treatment will initially mimic the excitation conditions used for in-vitro studies and will be revised according to the results of the evaluation of photoactivated antitumor efficacy of the polymer nanoparticles, while the schedule will parallel that of nanoparticle administration. Endpoints for antitumor effectiveness are tumor size and tumor volume. Tumor sizes will be measured by calipers 3 times per week until tumors reach 15% of the animal's body weight. At that point animals will be euthanized. Tumor sizes will be converted to weight as mg=[Width$^2$×Length]/2 (where the width is the shortest measurement in millimeters), and the mean value of tumor weight will be calculated for each treatment group. Tumor volumes will be calculated as $V=0.52 \times a^2 \times b$ (where a is smallest superficial diameter and b is largest superficial diameter). The tumor volume on a given day of measurement (Vt) relative to the start of the treatment (Vo) is designated as Vr, and will be calculated as Vr=Vt/Vo.

The percent tumor growth inhibition (% TGI) for each treatment will be determined by % TGI=100×(1−Wt/Wc), where We is weight of tumor in the control group and Wt is weight found in each treatment group. Differences among treatment groups will be statistically analyzed using at test (P>0.05). A % TGI>60% for the test agent will be suggestive of antitumor effect. In cases where tumor growth is strongly suppressed, animals will be monitored for up to 3 months.

Nanoparticle clearance from the animal body at the end of experiments is evaluated. It is known that biodistribution and clearance are critically related to nanoparticle size.[1] Therefore, the inventors fabricate the polymer nanoparticles using a method that allows for narrow size distributions. The distribution profiles are studied for the organs that are mainly responsible for clearance, i.e. the liver, spleen, and kidneys, by ex-vivo fluorescence imaging of the resected tissues. These data are correlated with the nanoparticle size and nanoparticle size distribution.

Statistical analysis of the significance in observed differences between treatment groups is conducted. Tumor volumes of all the treatment groups is compared using Fisher's test. The statistical analysis are carried out by use of StudyResult (CreoStat HB, Sweden) and PS (Vanderbilt University). The inventors will also perform analysis of variance (ANOVA) with Bonferroni corrected multiple-comparison post-test (INSTAT software, La Jolla, USA). In each case, p<0.05 will be taken as statistically significant.

REFERENCES (1) Choi, H. S.; Liu, W. H.; Liu, F. B.; Nasr, K.; Misra, P.; Bawendi, M. G.; Frangioni, J. V. *Nature Nanotechnology* 2010, 5, 42.
(2) Droge, W. *Physiological Reviews* 2002, 82, 47.
(3) Valko, M.; Leibfritz, D.; Moncol, J.; Cronin, M. T. D.; Mazur, M.; Telser, J. *International Journal of Biochemistry & Cell Biology* 2007, 39, 44.
(4) Valko, M.; Rhodes, C. J.; Moncol, J.; Izakovic, M.; Mazur, M. *Chemico-Biological Interactions* 2006, 160, 1.
(5) Wallace, D. C. A mitochondrial paradigm of metabolic and degenerative diseases, aging, and cancer: A dawn for evolutionary medicine. In *Annual Review of Genetics*, 2005; Vol. 39; pp 359.
(6) Cantley, L. C. *Science* 2002, 296, 1655.
(7) Downward, J. *Nature Reviews Cancer* 2003, 3, 11.
(8) Karin, M.; Cao, Y. X.; Greten, F. R.; Li, Z. W. *Nature Reviews Cancer* 2002, 2, 301.
(9) Wilhelm, S. M.; Carter, C.; Tang, L. Y.; Wilkie, D.; McNabola, A.; Rong, H.; Chen, C.; Zhang, X. M.; Vincent, P.; McHugh, M.; Cao, Y. C.; Shujath, J.; Gawlak, S.; Eveleigh, D.; Rowley, B.; Liu, L.; Adnane, L.; Lynch, M.; Auclair, D.; Taylor, I.; Gedrich, R.; Voznesensky, A.; Riedl, B.; Post, L. E.; Bollag, G.; Trail, P. A. *Cancer Research* 2004, 64, 7099.
(10) Manning, B. D.; Cantley, L. C. *Cell* 2007, 129, 1261.
(11) Vivanco, I.; Sawyers, C. L. *Nature Reviews Cancer* 2002, 2, 489.
(12) Engelman, J. A.; Zejnullahu, K.; Mitsudomi, T.; Song, Y.; Hyland, C.; Park, J. O.; Lindeman, N.; Gale, C.-M.; Zhao, X.; Christensen, J.; Kosaka, T.; Holmes, A. J.; Rogers, A. M.; Cappuzzo, F.; Mok, T.; Lee, C.; Johnson, B. E.; Cantley, L. C.; Janne, P. A. *Science* 2007, 316, 1039.
(13) Hennessy, B. T.; Smith, D. L.; Ram, P. T.; Lu, Y. L.; Mills, G. B. *Nature Reviews Drug Discovery* 2005, 4, 988.
(14) Elstrom, R. L.; Bauer, D. E.; Buzzai, M.; Karnauskas, R.; Harris, M. H.; Plas, D. R.; Zhuang, H. M.; Cinalli, R. M.; Alavi, A.; Rudin, C. M.; Thompson, C. B. *Cancer Research* 2004, 64, 3892.
(15) Nogueira, V.; Park, Y.; Chen, C.-C.; Xu, P.-Z.; Chen, M.-L.; Tonic, I.; Unterman, T.; Hay, N. *Cancer Cell* 2008, 14, 458.

(16) Robey, R. B.; Hay, N. *Oncogene* 2006, 25, 4683.
(17) Tsuruo, T.; Naito, M.; Tomida, A.; Fujita, N.; Mashima, T.; Sakamoto, H.; Haga, N. *Cancer Science* 2003, 94, 15.
(18) Fariss, M. W.; Chan, C. B.; Patel, M.; Van Houten, B.; Orrenius, S. *Molecular Interventions* 2005, 5, 94.
(19) Alscher, R. G.; Donahue, J. L.; Cramer, C. L. *Physiologia Plantarum* 1997, 100, 224.
(20) Baynes, J. W. *Diabetes* 1991, 40, 405.
(21) Baynes, J. W.; Thorpe, S. R. *Diabetes* 1999, 48, 1.
(22) Blokhina, O.; Virolainen, E.; Fagerstedt, K. V. *Annals of Botany* 2003, 91, 179.
(23) Dandona, P.; Thusu, K.; Cook, S.; Snyder, B.; Makowski, J.; Armstrong, D.; Nicotera, T. *Lancet* 1996, 347, 444.
(24) Floyd, R. A. *Proceedings of the Society for Experimental Biology and Medicine* 1999, 222, 236.
(25) Galvez-Valdivieso, G.; Mullineaux, P. M. *Physiologia Plantarum*, 138, 430.
(26) Hancock, J. T.; Desikan, R.; Neill, S. J. *Biochemical Society Transactions* 2001, 29, 345.
(27) Hensley, K.; Robinson, K. A.; Gabbita, S. P.; Salsman, S.; Floyd, R. A. *Free Radical Biology and Medicine* 2000, 28, 1456.
(28) Kamata, H.; Hirata, H. *Cellular Signalling* 1999, 11, 1.
(29) Liou, G. Y.; Storz, P. *Free Radical Research*, 44, 479.
(30) Riley, P. A. *International Journal of Radiation Biology* 1994, 65, 27.
(31) Simonian, N. A.; Coyle, J. T. *Annual Review of Pharmacology and Toxicology* 1996, 36, 83.
(32) Thannickal, V. J.; Fanburg, B. L. *American Journal of Physiology-Lung Cellular and Molecular Physiology* 2000, 279, L1005.
(33) Zhou, H.; Liu, X.; Liu, L.; Yang, Z.; Zhang, S.; Tang, M.; Tang, Y.; Dong, Q.; Hu, R. *Journal of International Medical Research* 2009, 37, 1897.
(34) Huang, P.; Trachootham, D.; Alexandre, J. *Nature Reviews Drug Discovery* 2009, 8, 579.
(35) Huang, P.; Trachootham, D.; Zhou, Y.; Zhang, H.; Demizu, Y.; Chen, Z.; Pelicano, H.; Chiao, P. J.; Achanta, G.; Arlinghaus, R. B.; Liu, J. S. *Cancer Cell* 2006, 10, 241.
(36) Chan, W.-H.; Shiao, N.-H.; Lu, P.-Z. *Toxicology Letters* 2006, 167, 191.
(37) Chen, J.-Y.; Lee, Y.-M.; Zhao, D.; Mak, N.-K.; Wong, R. N.-S.; Chan, W.-H.; Cheung, N.-H. *Photochemistry and Photobiology* 2010, 86, 431.
(38) Cho, S. J.; Maysinger, D.; Jain, M.; Roder, B.; Hackbarth, S.; Winnik, F. M. *Langmuir* 2007, 23, 1974.
(39) Ito, S.; Miyoshi, N.; Degraff, W. G.; Nagashima, K.; Kirschenbaum, L. J.; Riesz, P. *Free Radical Research* 2009, 43, 1214.
(40) Li, K. G.; Chen, J. T.; Bai, S. S.; Wen, X.; Song, S. Y.; Yu, Q.; Li, J.; Wang, Y. Q. *Toxicology in Vitro* 2009, 23, 1007.
(41) Park, E.-J.; Yi, J.; Chung, Y.-H.; Ryu, D.-Y.; Choi, J.; Park, K. *Toxicology Letters* 2008, 180, 222.
(42) Premanathan, M.; Karthikeyan, K.; Jeyasubramanian, K.; Manivannan, G. *Nanomedicine-Nanotechnology Biology and Medicine* 2011, 7, 184.
(43) Wu, Y.-N.; Yang, L.-X.; Shi, X.-Y.; Li, I. C.; Biazik, J. M.; Ratinac, K. R.; Chen, D.-H.; Thordarson, P.; Shieh, D.-B.; Braet, F. *Biomaterials* 2011, 32, 4565.
(44) Xue, C.; Wu, J.; Lan, F.; Liu, W.; Yang, X.; Zeng, F.; Xu, H. *Journal of Nanoscience and Nanotechnology* 2010, 10, 8500.
(45) Zhang, Q.; Yang, W.; Man, N.; Zheng, F.; Shen, Y.; Sun, K.; Li, Y.; Wen, L.-P. *Autophagy* 2009, 5, 1107.
(46) Zhang, Y.; Chen, W.; Wang, S.; Liu, Y.; Pope, C. *Journal of Biomedical Nanotechnology* 2008, 4, 432.
(47) Bridot, J. L.; Faure, A. C.; Laurent, S.; Riviere, C.; Billotey, C.; Hiba, B.; Janier, M.; Josserand, V.; Coll, J. L.; Vander Elst, L.; Muller, R.; Roux, S.; Perriat, P.; Tillement, O. *J Am Chem Soc* 2007, 129, 5076.
(48) Cheon, J.; Lee, J. H. *Accounts of Chemical Research* 2008, 41, 1630.
(49) Kim, J.; Piao, Y.; Hyeon, T. *Chemical Society Reviews* 2009, 38, 372.
(50) Mulder, W. J. M.; Strijkers, G. J.; Van Tilborg, G. A. F.; Cormode, D. P.; Fayad, Z. A.; Nicolay, K. *Accounts of Chemical Research* 2009, 42, 904.
(51) Hu, Z. J.; Tenery, D.; Bonner, M. S.; Gesquiere, A. J. *Journal Of Luminescence* 2010, 130, 771.
(52) Tenery, D.; Worden, J. G.; Hu, Z. J.; Gesquiere, A. J. *Journal of Luminescence* 2009, 129, 423.
(53) Tenery, D.; Gesquiere, A. J. *Chemical Physics* 2009, 365, 138.
(54) Tenery, D.; Gesquiere, A. J. *Chemphyschem* 2009, 10, 2449.
(55) Hu, Z. J.; Gesquiere, A. J. *Chemical Physics Letters* 2009, 476, 51.
(56) Gesquiere, A. J.; Tenery, D.; Hu, Z. J. *Spectroscopy* 2008, 23, 32.
(57) http://health.usnews.com/best-hospital/rankings/cancer 2011, *US News*.
(58) *American Cancer Society* 2011.
(59) Diamandopoulus, G. T. *Anticancer Res.* 1996, 16, 1596.
(60) Sayes, C. M.; Gobin, A. M.; Ausman, K. D.; Mendez, J.; West, J. L.; Colvin, V. L. *Biomaterials* 2005, 26, 7587.
(61) Green, M.; Howes, P.; Levitt, J.; Suhling, K.; Hughes, M. *J Am Chem Soc* 2010, 132, 3989.
(62) Siddiquee, K.; Zhang, S.; Guida, W. C.; Blaskovich, M. A.; Greedy, B.; Lawrence, H. R.; Yip, M. L. R.; Jove, R.; McLaughlin, M. M.; Lawrence, N. J.; Sebti, S. M.; Turkson, J. *Proceedings of the National Academy of Sciences of the United States of America* 2007, 104, 7391.
(63) Turkson, J.; Zhang, S. M.; Palmer, J.; Kay, H.; Stanko, J.; Mora, L. B.; Sebti, S.; Yu, H.; Jove, R. *Molecular Cancer Therapeutics* 2004, 3, 1533.
(64) Grimland, J. L.; Wu, C.; Ramoutar, R. R.; Brumaghim, J. L.; McNeill, J. *Nanoscale* 2011, 3, 1451.
(65) Harewood, G. C.; Baron, T. H.; Rumalla, A.; Wang, K. K.; Gores, G. J.; Stadheim, L. M.; De Groen, P. C. J. *Gastroenterol. Hepatol.* 2005, 20, 415.
(66) Mlkvy, P.; Messmann, H.; Regula, J.; Conio, M.; Pauer, M.; Millson, C. E.; MacRobert, A. J.; Bown, S. G. *Neoplasma* 1998, 45, 157.
(67) Overholt, B. F.; Panjehpour, M.; Haydek, J. M. *Gastrointestinal Endoscopy* 1999, 49, 1.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The teachings of any patents, patent applications, technical or scientific articles or other references are incorporated herein in their entirety to the extent not inconsistent with the teachings herein.

What is claimed is:

1. A method for treating ovarian cancer in a subject, said method comprising administering a therapeutically effective amount of poly[2-methoxy-5-(2-ethylhexyl-oxy)-p-phenylenevinylene]/Methoxycarbonylpropyl-1-phenyl-[6.6]C61 (MEH-PPV/PCBM) composite conjugated polymer nanoparticles to said subject such that ovarian cancer cells uptake said nanoparticles; and exposing said ovarian cancer cells to at least 60 J/cm$^2$ of light.

2. The method of claim 1, wherein said nanoparticles are produced via an emulsion process.

3. The method of claim 1, wherein said MEH-PPV/PCBM composite conjugated polymer nanoparticles create reactive oxygen species (ROS) upon photoactivation.

4. A method for treating ovarian or lung cancer resulting in a reduction in bulk tumor size and/or a reduction in cancer cells in a subject, the method comprising administering to said subject in need thereof a therapeutically effective regimen, the regimen comprising the administration of a therapeutic agent to the human subject such that the cancer cells uptake the therapeutic agent, and exposing the cancer cells to at least 120 J/cm$^2$ of light, wherein the regimen results in at least a 10% reduction in cancer cells in said subject, and wherein said therapeutic agent is MEH-PPV/PCBM composite conjugated polymer nanoparticles.

5. A method for treating ovarian or lung cancer in a subject, said method comprising administering a therapeutically effective amount of MEH-PPV conjugated polymer nanoparticles or MEH-PPV/PCBM composite conjugated polymer nanoparticles to said subject such that cancer cells uptake said nanoparticles; and exposing said cancer cells to at least 120 J/cm$^2$ of light.

* * * * *